United States Patent [19]

Ohashi et al.

[11] Patent Number: 4,695,580

[45] Date of Patent: Sep. 22, 1987

[54] PHENYLSERINE DERIVATIVES AND PROCESSES FOR PREPARING THE SAME

[75] Inventors: Naohito Ohashi, Newton, Mass.; Shoji Nagata, Takarazuka, Japan; Masashi Nakatsuka, Osaka, Japan; Kikuo Ishizumi, Toyonaka, Japan; Junki Katsube, Toyonaka, Japan; Shunji Aono, Toyonaka, Japan; Teruo Sakurama, Toyonaka, Japan

[73] Assignee: Sumitomo Pharmaceuticals Company, Ltd., Osaka, Japan

[21] Appl. No.: 683,430

[22] Filed: Dec. 19, 1984

[30] Foreign Application Priority Data

Dec. 20, 1983 [JP] Japan ............................ 58-241601

[51] Int. Cl.[4] .................. A61K 31/40; A61K 31/165; A61K 31/215; C07D 209/08; C07D 209/44; C07D 295/18
[52] U.S. Cl. .................................. 514/412; 514/414; 514/415; 514/416; 514/422; 514/423; 540/520; 544/162; 544/391; 546/146; 546/226; 546/309; 548/251; 548/452; 548/455; 548/465; 548/467; 548/482; 548/517; 548/518; 548/525; 548/526; 548/527; 548/533; 548/536; 548/540; 560/27; 560/29; 560/39; 562/448; 564/165
[58] Field of Search ............... 548/540, 452, 455, 465, 548/470, 517, 518, 526, 527, 533, 540, 467, 482, 525, 536; 514/423, 412, 415, 414, 422

[56] References Cited

U.S. PATENT DOCUMENTS

| | | | |
|---|---|---|---|
| 2,654,754 | 10/1953 | Bruce et al. | 548/540 X |
| 2,851,494 | 9/1958 | Ehrhart et al. | 548/540 X |
| 4,330,558 | 5/1982 | Suzuki et al. | 424/319 |
| 4,497,826 | 2/1985 | Narabayashi et al. | 514/567 |

OTHER PUBLICATIONS

Helv. Chim. Acta., 1975, vol. 58, pp. 147–162, Hegedus et al.

*Primary Examiner*—Joseph Paul Brust
*Attorney, Agent, or Firm*—Birch, Stewart, Kolasch & Birch

[57] ABSTRACT

Novel phenylserine derivatives of the formula:

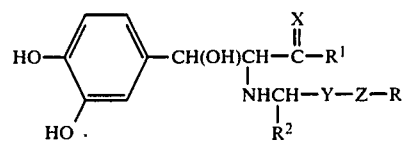

and pharmaceutically acceptable acid addition salts thereof, pharmaceutical compositions, and a process for preparing the compounds are disclosed. The phenylserine derivatives and pharmaceutically acceptable acid addition salts are capable of inhibiting the biosynthesis of leucotrienes and/or antagonistic activity against SRS-A and hence are useful for prophylaxis and treatment of various allergic diseases (e.g. bronchial asthma, allergic nasitis, urticaria), ischemic heart diseases, ischemic encephalopathy, inflammation, or the like.

11 Claims, No Drawings

PHENYLSERINE DERIVATIVES AND PROCESSES FOR PREPARING THE SAME

The present invention relates to novel phenylserine derivatives and processes for preparing the same. More particularly, the present invention relates to phenylserine derivatives of the formula:

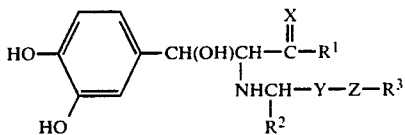

wherein $R^1$ is a group of the formula: $-OR^4$ or $-NR^5R^6$; $R_4$ is hydrogen atom, a $C_1$-$C_4$ alkyl, a $C_5$-$C_6$ cycloalkyl, carbamoyl, an N-($C_1$-$C_4$ alkyl)carbamoyl, a carbo($C_1$-$C_4$ alkoxy)methyl, carbamoylmethyl, or an N,N-di($C_1$-$C_4$ alkyl)carbamoylmethyl; $R_5$ is hydrogen atom, a $C_1$-$C_4$ alkyl, a $C_5$-$C_6$ cycloalkyl, an unsubstituted phenyl, a phenyl substituted by carboxyl or a carbo($C_1$-$C_4$)alkoxy, pyridyl, tetraxzolyl, a hydroy($C_2$-$C_4$)-alkyl, a $C_1$-$C_4$ alkoxy($C_2$-$C_4$)alkyl, a di($C_1$-$C_4$ alkyl) amino($C_2$-$C_4$)alkyl, amino, acetylamino, or isopropylidenamino; $R^6$ is hydrogen atom, or a $C_1$-$C_4$ alkyl; or $R^5$ and $R^6$ combine together with adjacent nitrogen atom to form a cyclic amino group of the formula:

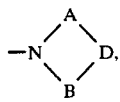

wherein A and B are the same or different and are each an unsubstituted straight chain $C_1$-$C_3$ alkylene, a straight chain $C_1$-$C_3$ alkylene substitu by a member selected from a $C_1$-$C_4$ alkyl, carboxyl, a carbo($C_1$-$C_4$)alkoxy, a hydroxy($C_1$-$C_4$)alkyl and phenyl, or a single bond, and D is a $C_1$-$C_4$alkylene, 1,2- or 1,4-cyclohexylidene, 1,2-benzo, oxa, or an imino substituted by a $C_1$-$C_4$ alkyl or phenyl;

$>C=X$ is $>CO$, $>CH_2$, or $>C(C_1$-$C_4$ alkyl$)_2$;

$R^2$ is hydrogen atom, a $C_1$-$C_4$ alkyl, or phenyl;

$R^3$ is hydrogen atom, a $C_1$-$C_4$ alkyl, a $C_5$-$C_6$ cycloalkyl, an unsubstituted phenyl, a phenyl having one or more substituents selected from a $C_1$-$C_4$ alkyl, hydroxy, a $C_1$-$C_4$ alkoxy, a halogen, trifluoromethyl, a di ($C_1$-$C_4$ alkyl) amino, and methylenedioxy, naphthyl, pyridyl, furyl, thienyl, pyrrolyl, indolyl, or ferrocenyl;

Y is a single bond, an unsubstituted $C_1$-$C_4$ alkylene, or a $C_1$-$C_4$ alkylene substituted by a $C_1$-$C_4$ alkyl or phenyl;

Z is a single bond, oxa, thia, a $C_1$-$C_4$ alkylimino, or $-CONH-$, or the group $Z-R^3$ forms 1,4-benzodioxanyl group, or the group $R^2-CH-Y-Z-R^3$ forms a $C_5$-$C_6$ cycloalkyl or tetrahydronaphthyl group; or acid addition salts thereof, and processes for preparing the compounds.

The phenylserine nucleus of the compounds [I] contains two asymmetric carbons, and hence, the compounds [I] include four stereo- and/or optical isomers, such as L-threo, D-threo, L-erythro and D-erythro isomers. The present invention includes all these isomers and also a mixture thereof, such as DL-threo and DL-erythro isomers.

In the above formula [I], the "$C_1$-$C_4$ alkyl" includes straight or branched chain alkyl groups, such as methyl, ethyl, n-propyl, n-butyl, isopropyl, isobutyl, etc. The "$C_5$-$C_6$ cycloalkyl" includes, for example, cyclopentyl and cyclohexyl. The "N-($C_1$-$C_4$ alkyl)carbamoyl" includes, for example, N-methylcarbamcyl, etc. The "carbo($C_1$-$C_4$ alkoxy)methyl" includes, for example, ethoxycarbonylmethyl, etc. The "N,N-di($C_1$-$C_4$ alkyl)-carbamoylmethyl" includes, for example, N,N-dimethylcarbamoylmethyl, N,N-diethylcarbamoylmethyl, etc. The "carbo($C_1$-$C_4$)alkoxy" includes, for example, carbomethoxy, carboethoxy, etc. The "hydroxy($C_2$-$C_4$)alkyl" includes, for example, hydroxyethyl, hydroxypropyl, etc. The "$C_1$-$C_4$ alkoxy($C_2$-$C_4$)alkyl" includes, for example, methoxyethyl, ethoxyethyl, isopropoxyethyl, methoxypropyl, etc. The "di($C_1$-$C_4$ alkyl)amino($C_2$-$C_4$)alkyl" includes, for example, dimethylaminoethyl, diethylaminoethyl, dimethylaminopropyl, etc. The "hydroxy($C_1$-$C_4$)alkyl" includes, for example, hydroxymethyl, hydroxyethyl, hydroxypropyl, etc. The "straight chain $C_1$-$C_3$ alkylene" includes, for example, methylene, ethylene, and trimethylene. The "$C_1$-$C_4$ alkylene" includes, for example, xethylene, ethylene, trimethylene, tetramethylene, etc. "$C_1$-$C_4$ alkoxy" includes, for example, methoxy, ethoxy, isopropoxy, etc. The "di($C_1$-$C_4$ alkyl)amino" includes, for example, dimethylamino, diethylamino, dipropylamino, etc. The "$C_1$-$C_4$ alkylimino" includes, for example, methylimino, ethylimino, n-propylimino, etc. The "halogen atom" includes, for example, fluorine, chlorine, bromine, etc.

Among the compounds [I], the preferred compounds are those compounds of the formula [I] wherein when $>C=X$ is $>CO$, $R^1$ is a group of the formula: $-OR^4$ or $-NR^5R^6$; $R^4$ is hydrogen atom, a $C_1$-$C_4$ alkyl, a $C_5$-$C_6$ cycloalkyl, a carbo($C_1$-$C_2$ alkoxy)methyl, carbamoylmethyl, or an N,N-di($C_1$-$C_2$ alkyl)carbamoylmethyl; $R^5$ is hydrogen atom, a $C_1$-$C_4$ alkyl, a $C_5$-$C_6$ cycloalkyl, an unsubstituted phenyl, a phenyl substituted by carboxyl or a carbo($C_1$-$C_2$)alkoxy, pyridyl, tetrazolyl, hydroxyethyl, methoxyethyl, dimethylaminoethyl, amino, acetylamino, or isopropylidenamino; $R^6$ is hydrogen atom, or a $C_1$-$C_2$ alkyl; or $R^5$ and $R^6$ combine together with adjacent nitrogen atom to form a cyclic amino group of the formula:

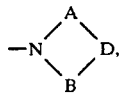

wherein A and B are the same or different and are each an unsubstituted straight chain $C_1$-$C_3$ alkylene, a straight chain $C_1$-$C_3$ alkylene substituted by a member selected from methyl, carboxyl, carbomethoxy, hydroxymethyl and phenyl, or a single bond, and D is a $C_1$-$C_2$ alkylene, 1,2- or 1,4-cyclohexylidene, 1,2-benzo, oxa, or an imino substituted by methyl or phenyl; and when $>C=X$ is $>CH_2$, or $>C(methyl)_2$, $R^1$ is $-OR^4$ or $-NR^5R^6$, and $R^4$ is hydrogen atom, carbamoyl, or N-methylcarbamoyl, and $-NR^5R^6$ is amino or pyrrolidino;

$R^2$ is hydrogen atom, a $C_1$-$C_2$ alkyl, or phenyl;

$R^3$ is hydrogen atom, a $C_1$-$C_3$ alkyl, cyclohexyl, an unsubstituted phenyl, a phenyl having one or more substituents selected from a $C_1$-$C_4$ alkyl, hydroxy, methoxy, dimethylamino, trifluoromethyl, methylenedioxy, and a halogen atom, naphthyl, pyridyl, furyl, thienyl, pyrrolyl, indolyl, or ferrocenyl;

Y is a single bond, an unsubstituted $C_1$-$C_4$ alkylene, or a $C_1$-$C_4$ alkylene substituted by methyl or phenyl;

Z is a single bond, oxa, methylimino, or —CONH—, or the group Z—$R^3$ forms 1,4-benzodioxanyl group, or the group $R^2$—CH—Y—Z—$R^3$ forms tetrahydronaphthyl group.

More preferred compounds are those compounds of the formula [I] wherein when >C=X is >CO, $R^1$ is a group of the formula: —$OR^4$ or —$NR^5R^6$; $R^4$ is a $C_1$-$C_4$ alkyl, or a carbo($C_1$-$C_2$ alkoxy)methyl; $R^5$ is hydrogen atom, methyl, ethyl, or amino; $R^6$ is hydrogen atom or methyl; or $R^5$ and $R^6$ combine together with adjacent nitrogen atom to form a cyclic amino group of the formula:

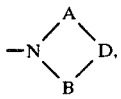

wherein A and B are the same or different and are each an unsubstituted straight chain $C_1$-$C_3$ alkylene, a straight chain $C_1$-$C_3$ alkylene substituted by a member selected from methyl, carbomethoxy, hydroxymethyl and phenyl, or a single bond, and D is methylene, ethylene, 1,2- or 1,4-cyclohexylidene, or 1,2-benzo; and when >C=X is >$CH_2$, or >C(methyl)$_2$, $R^1$ is —$OR^4$ or —$NR^5R^6$, and $R^4$ is hydrogen atom or carbamoyl, and —$NR^5R^6$ is pyrrolidino;

$R^2$ is hydrogen atom, methyl, or phenyl;

$R^3$ is a $C_1$-$C_3$ alkyl, cyclohexyl, an unsubstituted phenyl, a phenyl having one or more substituents selected from a $C_1$-$C_4$ alkyl, hydroxy, methoxy, dimethylamino, trifluoromethyl, methylenedioxy, and a halogen atom, naphthyl, pyridyl, furyl, thienyl, pyrrolyl, or indolyl;

Y is a single bond or an unsulstituted straight chain $C_1$-$C_4$ alkylene;

Z is a single bond, oxa, methylimino, or —CONH—, or the group $R^2$—CH—Y—Z—$R^3$ forms tetrahydronaphthyl group.

The most preferred compounds are those compounds of the formula [I] wherein when >C=X is >CO, $R^1$ is a group of the formula: —$OR^4$ or —$NR^5R^6$; $R^4$ is a $C_1$-$C_4$ alkyl, or a carbo($C_1$-$C_2$ alkoxy)methyl; $R^5$ is hydrogen atcm, methyl, ethyl, or amino; $R^6$ is hydrogen atom or methyl; or $R^5$ and $R^6$ combine together with adjacent nitrogen atom to form a cyclic amino group of the formula:

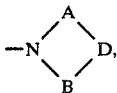

wherein A and B are the same or different and are each an unsubstituted straight chain $C_1$-$C_3$ alkylene, a straight chain $C_1$-$C_3$ alkylene substituted by carbomethoxy, hydroxymethyl or phenyl, or a single bond, and D is methylene, ethylene, 1,2-cyclohexylidene, or 1,2-benzo; and when >C=X is >$CH_2$, or >C(methyl)$_2$, $R^1$ is —$OR^4$, and $R^4$ is hydrogen atom or carbamoyl;

$R^2$ is hydrogen atom, methyl, or phenyl;

$R^3$ is a $C_1$-$C_3$ alkyl, cyclohexyl, an unsubstituted phenyl, a phenyl having one or more substituents selected from a $C_1$-$C_4$ alkyl, hydroxy, methoxy, dinethylamino, trifluoromethyl, methylenedioxy, and a halogen atom, naphthyl, pyridyl, furyl, thienyl, or pyrrolyl;

Y is a single bond or a straight chain $C_1$-$C_4$ alkylene;

Z is a single bond, oxa, methylimino, or —CONH—, or the groug $R^2$—CH—Y—Z—$R^3$ forms tetrahydronaphthyl group.

The compounds [I] of the present invention may form pharmaceutically acceptable acic addition salts with various acids, such as inorganic acids (e.g. hydrochloric acid, hydrobromic acid, sulfuric acid, phosphoric acid, etc.) or organic acids (e.g. acetic acid, propionic acid, butyric acid, tartaric acid, citric acid, maleic acid, fumaric acid, methanesulfonic acid, etc.)

It has recently been known that various leucotrienes produced from arachidonic acid by biosynthesis induce contraction of various smooth muscles and further promotion of permeability of peripheral blood vessels, and particularly that SRS-A (slow reacting substance of anaphyraxis) is a chemical mediator in inflammation diseases and hence causes bronchial asthma, allergic diseases, and various diseases in the circulation system [cf. Gendai-iryo 12, pp. 909, 1029, 1065 and 1105 (1980)].

Based on such knowledge, the present inventors have conducted intense studies on new compounds which are effective on the diseases induced by leucotrienes and then have found that the compounds [I] of the present invention inhibit the biosynthesis of leucotrienes and/or antagonistic activity against SRS-A and hence are useful for prophylaxis and treatment of various allergic diseases (e.g. bronchial asthma, allergic nasitis, urticaria), ischemic heart disease, ischemic encephalopathy, inflammation, or the like.

The compounds [I] of the present invention and non-toxic salts thereof are usually used in conventional pharmaceutical preparations suitable for oral or parenteral administration. Preparations for oral administration include, for example, tablets, capsules, powders, granules, fine granules, and preparations for parenteral administration include, for example, injections for intravenous or intramuscular injection, aerosol preparation and intranasal preparation. The preparations can be prepared by using conventional carriers and diluents in a usual manner. The dose of the compounds of the present invention may vary depending on the administration method, age and sex of patients, severity of diseases, or the like, but is usually in a range of 0.1 mg to 1,000 mg, preferably 1 mg to 500 mg, per once.

The compounds [I] of the present invention can be prepared, for example, by the following processes.

(1) Process A:

A compound of the formula:

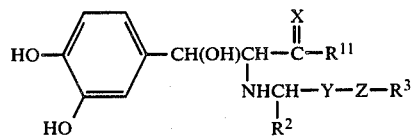

wherein >C=X is >CO, >$CH_2$, or >C($C_1$-$C_4$ alkyl)$_2$;

when >C=X is >CO, $R^{11}$ is a group of the formula: —$OR^4$ or —$NR^{51}R^6$; $R^4$ is hydrogen atom, a $C_1$-$C_4$ alkyl, a $C_5$-$C_6$ cycloalkyl, carbamoyl, an N-($C_1$-$C_4$ alkyl)carbamoyl, a carbo($C_1$-$C_4$ alkoxy)methyl, carbamoylmethyl, or an N,N-di($C_1$-$C_4$ alkyl)carbamoylmethyl; $R^{51}$ is hydrogen atom, a $C_1$-$C_4$ alkyl, a $C_5$-$C_6$ cycloalkyl, an unsubstituted phenyl, a phenyl substituted by carboxyl or a carbo($C_1$-$C_4$)alkoxy, pyridyl, tetrazolyl, a hydroxy($C_2$-$C_4$)alkyl, a $C_1$-$C_4$ alkoxy($C_2$-$C_4$)alkyl, a di($C_1$-$C_4$ alkyl)amino($C_2$-$C_4$)alkyl, or acetylamino; $R^6$ is hydrogen atom, or a $C_1$-$C_4$ alkyl; or $R^{51}$ and $R^6$ combine together with adjacent nitrogen atom to form a cyclic amino group of the formula:

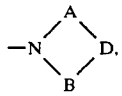

wherein A and B are the same or different and are each an unsubstituted straight chain $C_1$-$C_3$ alkylene, a straight chain $C_1$-$C_3$ alkylene substituted by a member selected from a $C_1$-$C_4$ alkyl, carboxyl, a carbo($C_1$-$C_4$)alkoxy, a hydroxy($C_1$-$C_4$)alkyl and phenyl, or a single bond, and D is a $C_1$-$C_4$ alkylene, 1,2- or 1,4-cyclohexylidene, 1,2-benzo, oxa, or an imino substituted by a $C_1$-$C_4$ alkyl or phenyl;

when $>C=X$ is $>CH_2$, or $>C(C_1$-$C_4$ alkyl$)_2$, $R_{11}$ is a group of the formula: $-OR^4$ or $-NR^{52}R^{61}$, and $R^4$ is as defined above, $R^{52}$ is a $C_1$-$C_4$ alkyl, a $C_5$-$C_6$ cycloalkyl, an unsubstituted phenyl, a phenyl substituted by carboxyl or a carbo($C_1$-$C_4$)alkoxy, pyridyl, tetrazolyl, a hydroxy($C_2$-$C_4$)alkyl, a $C_1$-$C_4$ alkoxy($C_2$-$C_4$)alkyl, a di($C_1$-$C_4$ alkyl)amino($C_2$-$C_4$)alkyl, or acetylamino; $R^{61}$ is a $C_1$-$C_4$ alkyl; or $R^{52}$ and $R^{61}$ combine together with adjacent nitrogen atom to form a cyclic amino group of the formula:

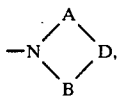

wherein A, B and D are as defined above, $R^2$ is hydrogen atom, a $C_1$-$C_4$ alkyl, or phenyl;

$R^3$ is hydrogen atom, a $C_1$-$C_4$ alkyl, a $C_5$-$C_6$ cycloalkyl, an unsubstituted phenyl, a phenyl having one or more substituents selected from a $C_1$-$C_4$ alkyl, hydroxy, a $C_1$-$C_4$ alkoxy, a halogen, trifluoromethyl, a di($C_1$-$C_4$ alkyl)amino, and methylenedioxy, naphthyl, pyridyl, frryl, thienyl, pyrrolyl, indolyl, or ferrocenyl;

Y is a single bond, an unsubstituted $C_1$-$C_4$ alkylene, or a $C_1$-$C_4$ alkylene substituted by a $C_1$-$C_4$ alkyl or phenyl;

Z is a single bond, oxa, thia, a $C_1$-$C_4$ alkylimino, or $-CONH-$, or the group $Z-R^3$ forms 1,4-benzodioxanyl group, or the group $R^2-CH-Y-Z-R^3$ forms a $C_5$-$C_6$ cycloalkyl or tetrahydronaphthyl group;

can be prepared by reacting a compound of the formula:

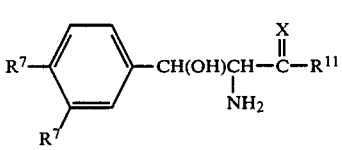

wherein X and $R^{11}$ are as defined above, and $R^7$ is hydroxy or benzyloxy, with a compound of the formula:

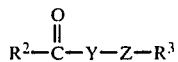

wherein $R^2$, Y, Z and $R^3$ are as defined above under reductive condition to obtain a compound of the formula:

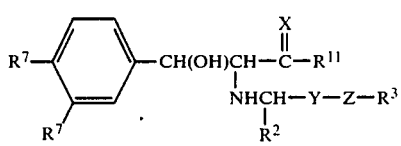

wherein X, $R^{11}$, $R^2$, $R^3$, $R^7$, Y and Z are as defined above, and when R7 is benzyloxy, subjecting the compound [IV] to a reaction for removal of the benzyl group.

The reaction of the compounds [II] and [III] under a reductive condition can be carried out in the presence of a boron reagent such as sodium borohydride, sodium cyanoborohydride, etc. or by catalytic reduction using a catalyst such as palladium on carbon, platinum oxide, etc.

The above reaction is carried out in a solvent such as alcohols (e.g. methanol, ethanol, isopropanol, etc.), aromatic solvents (e.g. benzene, toluene, etc.), ethers (e.g. dioxane, tetrahydrofuran, etc.), dimethylformamide, or the like, where the compound [III] is used in an amount of 1 to 3 moles to 1 mole of the compound [II]. When a boron reagent is used, it is used in an amount of 1 to 2 moles to 1 mole of the compound [III], and the reaction is carried out at ice-cooling to an elevated temperature. When the reaction is carried out by catalytic reduction, the catalyst is used in an amount of 0.01 to 0.5 parts by weight to 1 part by weight of the compound [II], and in this case, the reaction is carried out at an elevated temperature, or preferably at room temperature.

In case of the compound of the formula [II] wherein $R^7$ is benzyloxy, when the compound [II] is reacted with the compound [III] under catalytic reduction using for example a palladium catalyst, debenzylation reaction also proceeds together with N-alkylation to give a compound of the formula [IV] wherein $R^7$ is hydroxy, but on the other hand, when the reaction of the compound [II] and the compound [III] is carried out by using a platinum catalyst or a boron reagent, only N-alkylation reaction proceeds, and hence, the resulting compound is subjected to a catalytic reduction with a palladium catalyst at room temperature or an elevated temperature in order to remove the benzyl group.

The N-alkylation reaction under a reductive condition may alternatively be carried out by firstly reacting the compound [II] and the compound [III] to form a Schiff base, and then reducing the resulting compound with a boron reagent or subjecting to catalytic reduction with a palladium catalyst or a platinum catalyst.

(2) Process B:

Phenylserine derivatives of the formula:

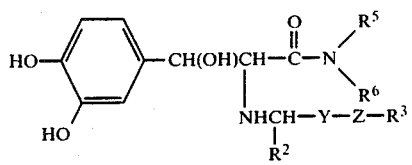 [Ib]

wherein $R^2$, $R^3$, $R^5$, $R^6$, Y and Z are the same as defined in the formula [I],
can be prepared by subjecting a compound of the formula:

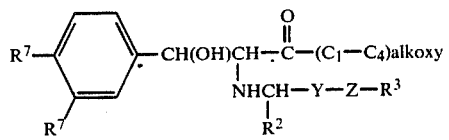 [V]

wherein $R^2$, $R^3$, $R^7$, Y and Z are as defined above, to a condensation reaction with an amine of the formula:

 [VI]

wherein $R^5$ and $R^6$ are as defined above, to give a compound of the formula:

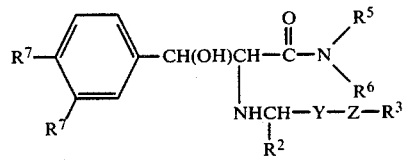 [VII]

wherein $R^2$, $R^3$, $R^5$, $R^6$, $R^7$, Y and Z are the same as defined above, and when $R^7$ is benzyloxy, subjecting the compound [VII] to the removal of benzyl group. The condensation reaction is carried out by reacting the compound [V] with an equimolar or excess amount of the compound [VI] in a solvent such as alcohols (e.g. methanol, isopropanol, etc.), ethers (e.g. tetrahydrofuran, dioxane, etc.), dimethylformamide, or dimethylsulfoxide, under cooling or preferably at an elevated temperature. The removal of benzyl group can be carried out in the same manner as described as to the above Process A.

(3) Process C:
Phenylserine derivatives of the formula:

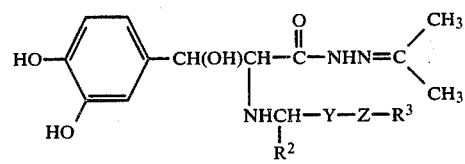 [Ic]

wherein $R^2$, $R^3$, Y and Z are the same as defined in the formula [I],
can be prepared by subjecting a compound of the formula:

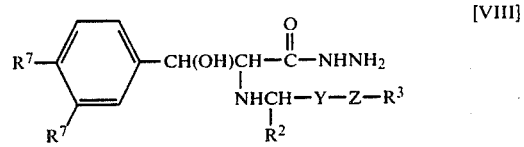 [VIII]

wherein $R^2$, $R^3$, $R^7$, Y and Z are as defined above, to a condensation reaction with acetone to give a compound of the formula:

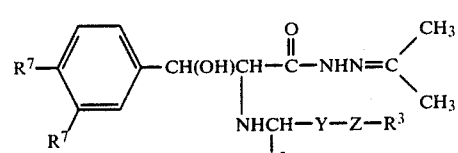 [IX]

wherein $R^2$, $R^3$, $R^7$, Y and Z are the same as defined above, and when $R^7$ is benzyloxy, subjecting the compound [IX] to the removal of a benzyl group.

The condensation reaction is carried out by reacting the compound [VIII] with an excess amount of acetone in a solvent such as ethers (e.g. dioxane, tetrahydrofuran, etc.), esters (e.g. an acetic acid ester, etc.) or halogenated alkanes (e.g. chloroform, dichloromethane, etc.) in the presence or absence of an acid catalyst such as silica gel or p-toluenesulfonic acid, at room temperature. Besides, the removal of the benzyl group can be carried out in the same manner as described above.

(4) Process D:
Phenylserine derivatives of the formula:

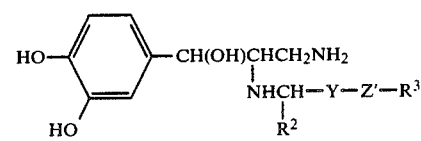 [Id]

wherein $R^2$, $R^3$ and Y are the same as defined in the formula [I], and Z' is a single bond, oxa, thia, a $C_1$-$C_4$ alkylimino, or the group Z'—$R^3$ forms 1,4-benzodioxanyl group, or the group $R^2$—CH—Y—Z'—$R^3$ forms a $C_5$-$C_6$ cycloalkyl or tetrahydronaphthyl group, can be prepared by subjecting a compound of the formula:

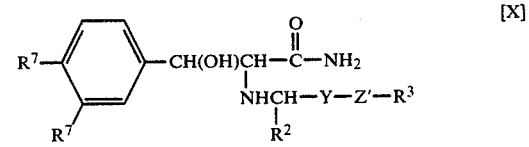 [X]

wherein $R^2$, $R^3$, $R^7$, Y and Z' are as defined above, to reduction with a metal hydride to give a compound of the formula:

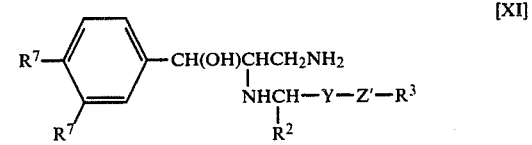 [XI]

wherein $R^2$, $R^3$, $R^7$, Y and Z' are the same as defined above, and when $R^7$ is benzyloxy, subjecting the compound [XI] to the removal of a benzyl group.

The reduction reaction is carried out by treating the compound [X] with an excess amount of a metal hydride, such as an aluminum hydride compound (e.g., aluminum hydride, lithium aluminum hydride, sodium bis(2-methoxyethoxy)aluminum hydride, etc.), or a boron hydride compound (e.g. diborane, etc.) in a solvent such as ethers (e.g. diethyl ether, tetrahydrofuran, etc.), in a conventional manner. Besides, the removal of the benzyl group can be carried out in the same manner as described above.

(5) Process E:

Phenylserine derivatives of the formula:

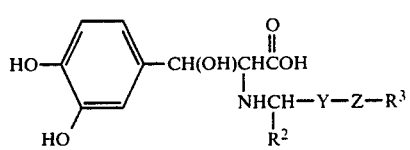
[Ie]

wherein $R^2$, $R^3$, Y and Z are the same as defined in the formula [I], can be prepared by subjecting a compound of the formula:

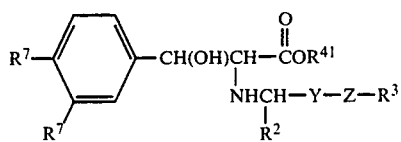
[XII]

wherein $R^2$, $R^3$, $R^7$, Y and Z are as defined above, and $R^{41}$ is a $C_1$–$C_4$ alkyl, a $C_5$–$C_6$ cycloalkyl, a carbo($C_1$–$C_4$ alkoxy)methyl, carbamoylmethyl, or N,N-di($C_1$–$C_4$ alkyl)carbamoylmethyl, to hydrolysis with an alkali such as sodium hydroxide or potassium hydroxide in a usual manner to give a compound of the formula:

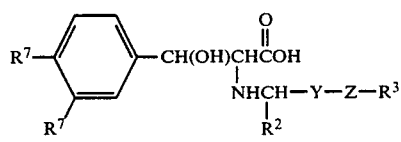
[XIII]

wherein $R^2$, $R^3$, $R^7$, Y and Z are the same as defined above, and when $R^7$ is benzyloxy, subjecting the compound [XIII] to the removal of a benzyl group.

In the above reaction, the removal of the benzyl group can be carried out in the same manner as described above.

(6) Process F:

Phenylserine derivatives of the formula:

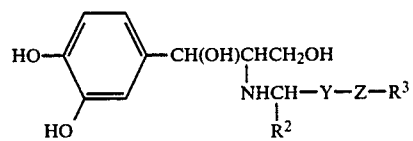
[If]

wherein $R^2$, $R^3$, Y and Z are the same as defined in the formula [I], can be prepared by reducing a compound of the formula [XII] as mentioned above to convert into a compound of the formula:

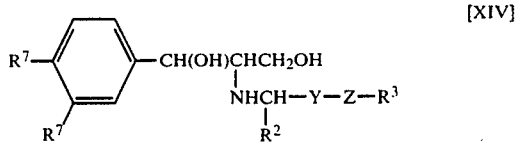
[XIV]

wherein $R^2$, $R^3$, $R^7$, Y and Z are the same as defined above, and when $R^7$ is benzyloxy, subjecting the compound [XIV] to the removal of a benzyl group.

The reduction of the compound [XII] is carried out by treating the compound with a reducing agent, such as calcium borohydride, lithium borohydride, etc. in an alcohol (e.g. ethanol, isopropanol, etc.) at a temperature of $-10°$ to $10°$ C. The reducing agent is used in an amount of 3 to 5 moles to 1 mole of the compound [XII]. Besides, the removal of the benzyl group can be carried out in the same manner as described hereinbefore.

(7) Process G:

Phenylserine derivatives of the formula:

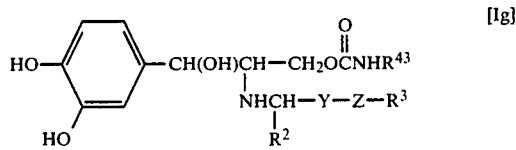
[Ig]

wherein $R^2$, $R^3$, Y and Z are the same as defined in the formula [I], and $R^{43}$ is hydrogen atom or a $C_1$–$C_4$ alkyl, can be prepared by reacting a compound of the formula [XIV] as mentioned hereinbefore with an alkali cyanate (e.g. sodium cyanate, potassium cyanate, etc.) or a compound of the formula:

$$R^{42}NCO \qquad [XV]$$

wherein $R^{42}$ is a $C_1$–$C_4$ alkyl, to give a compound of the formula:

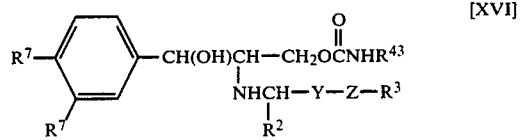
[XVI]

wherein $R^2$, $R^3$, $R^7$, $R^{43}$, Y and Z are the same as defined above, and when $R^7$ is benzyloxy, subjecting the compound [XVI] to the removal of a benzyl group.

The reaction of the compound [XIV] and the alkali cyanate or the compound [XV] is carried out by reacting 1 mole of the compound [XIV] with 1 to 2 moles of the alkali cyanate or the compound [XV] in a solvent such as ethers (e.g. dioxane, tetrahydrofuran, etc.), halogenated alkanes (e.g. chloroform, dichloromethane, etc.), aromatic hydrocarbons (e.g. benzene, toluene, etc.) or dimethylformamide in the presence of an excess amount of trifluoroacetic acid, at room temperature. Besides, the removal of the benzyl group can be carried out in the same manner as described hereinbefore.

(8) Process H:

Phenylserine derivatives of the formula:

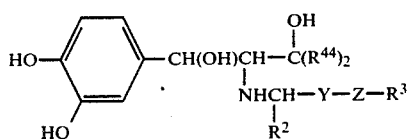 [Ih]

wherein $R^2$, $R^3$, Y and Z are the same as defined in the formula [I], and $R^{44}$ is a $C_1$–$C_4$ alkyl, can be prepared by reacting a compound of the formula [XII] or [XIII] as mentioned hereinbefore with a compound of the formula:

 [XVII]

wherein $R^{44}$ is as defined above and Hal means a halogen atom such as chlorine, bromine or iodine, to give a compound of the formula:

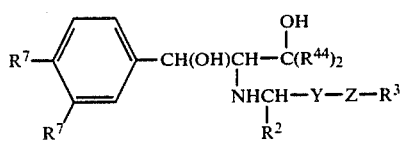 [XVIII]

wherein $R^2$, $R^3$, $R^7$, $R^{44}$, Y and Z are the same as defined above, and when $R^7$ is benzyloxy, subjecting the compound [XVIII] to the removal of a benzyl group.

The reaction of the compound [XII] or [XIII] and the compound [XVII] is carried out in a solvent such as toluene, diethyl ether, tetrahydrofuran, etc. under the same conditions as in the conventional Grignard reaction. Besides, the removal of the benzyl group can be carried out in the same manner as described hereinbefore.

(9) Process I:

A phenylserine derivative of the formula:

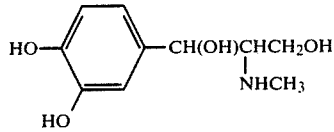 [Ii]

can be prepared by reducing a compound of the formula:

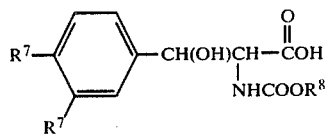 [XIX]

wherein $R^7$ is as defined above, and $R^8$ is a $C_1$–$C_4$ alkyl, or an aryl($C_1$–$C_4$)alkyl, with an aluminum hydride compound to give a compound of the formula:

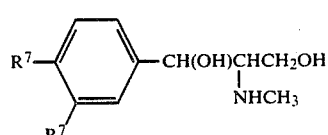 [XX]

wherein $R^7$ is as defined above, and when $R^7$ is benzyloxy, subjecting the compound [XX] to the removal of benzyl group.

The reduction reaction is carried out by treating the compound [XIX] with an excess amount of an aluminum hydride compound such as aluminum hydride, lithium aluminum hydride, sodium bis(2-methoxyethoxy)aluminum hydride, etc. in a solvent such as ethers (e.g. diethyl ether, tetrahydrofuran, etc.), in a conventional manner. Besides, the removal of the benzyl group can be carried out in the same manner as described hereinbefore.

The starting compound [II] used in the above processes can be prepared by the processes as shown in the following reaction schemes-I, -II, -III and -IV.

Reaction Scheme-I

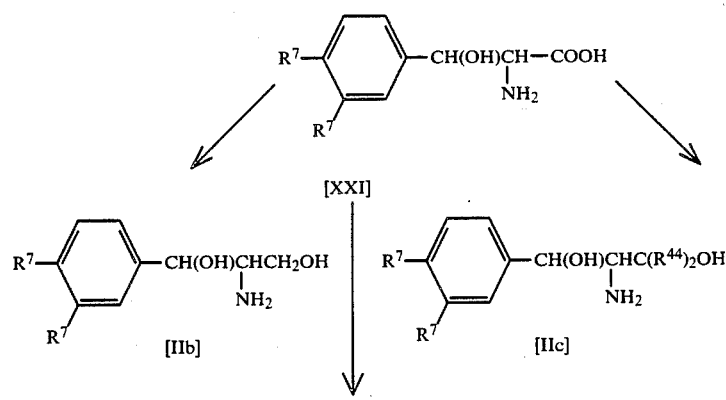

Reaction Scheme-I

-continued

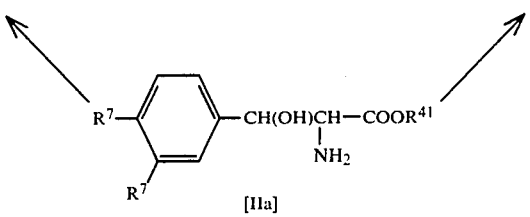

[IIa]

wherein $R^7$, $R^{41}$ and $R^{44}$ are as defined hereinbefore.

The starting compound [XXI] used in the above reaction is known (cf. Chem. Ber., 52, 1724 (1919); J. Chem. Soc., 658 (1947); Chem. Ber., 87, 892 (1954); J. Am. Chem. Soc., 76, 1322 (1954); Helv. Chim. Acta, 58, 157 (1975); and Japanese Patent Publication (unexamined) No. 49252/1975).

According to the reaction as shown in the above reaction scheme-I, the compound [XXI] is reacted with 2 to 4 molar equivalents of thionyl chloride in a lower alcohol (e.g. methanol, ethanol, etc.) at a temperature of −20° to 50° C. to give the compound [IIa]. Besides, the compound [XXI] is reacted with 1 to 2 molar equivalents of p-toluenesulfonyl chloride in a lower alcohol (e.g. methanol, ethanol, etc.) at room temperature or reflux temperature to give the compound [IIa].

The compound [IIb] can be prepared by reducing the compound [IIa] in the same manner as disclosed in Process F hereinbefore, or by treating the compound [XXI] or the compound [IIa] with an excess amount of an aluminum hydride compound (e.g. lithium aluminum hydride, sodium bis(2-methoxyethoxy)aluminum hydride, etc.) in an ether solvent (e.g. diethyl ether, tetrahydrofuran, etc.) in a usual manner.

The compound [IIc] can be prepared by subjecting the compound [XXI] or the compound [IIa] to a Grignard reaction in the same manner as disclosed in Process H hereinbefore.

In the compounds [IIa], [IIb] and [IIc], when the group $R^7$ is benzyloxy, these compounds can also be converted into the corresponding hydroxy compounds by removal of the benzyl group in the same manner as described in Process A hereinbefore.

The compound [XXII] is converted into the compound [XXIII] by reacting the compound [XXII] with a compound of the formula:

$$R^{41}-Hal \qquad [XXVIII]$$

$R^{41}$ wherein is as defined above, and Hal means a halogen atom such as chlorine, bromine or iodine, in an organic solvent (e.g. dimethylformamide) in the presence of a base such as organic bases (e.g. cyclohexylamine, etc.) or inorganic bases (e.g. sodium hydrogen carbonate, etc.) and sodium iodide, or alternatively by reacting the compound [XXII] with a compound of the formula:

$$HNR^{51}R^6 \qquad [XXIX]$$

wherein $R^{51}$ and $R^6$ are as defined hereinbefore, by conventional amidation processes. The amidation processes are carried out, for example, by reacting the compounds [XXII] with the compound [XXIX] in a solvent (e.g. dimethylformamide, methylene chloride, acetonitrile, etc.) in the presence of a condensing agent such as dicyclohexylcarbodiimide, or alternatively by reacting firstly the compound [XXII] with a molar equivalent of chloroformate (e.g. isobutyl chloroformate, isopropyl chloroformate, ethyl chloroformate, etc.) in a solvent such as a halogenated alkane (e.g. methylene chloride, chloroform, etc.), an ether (e.g. tetrahydrofuran, etc.), an ester (e.g. ethyl acetate, etc.) or dimethylformamide to convert into a mixed acid anhydride, and then reacting the mixed acid anhydride with the compound [XXIX].

Reaction Scheme-II

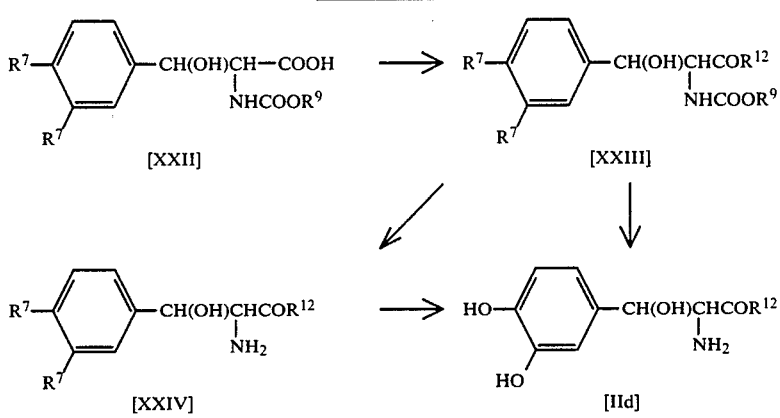

wherein $R^9$ is benzyl or t-butyl, $R^{12}$ is a group of the formula: $-OR^{41}$ or $-NR^{51}R^6$, and $R^6$, $R^7$, $R^{41}$, and $R^{51}$ are as defined hereinbefore.

In the compound [XXIII] obtained above, when the group $R^9$ is tert-butyl, the compound [XXIII] is reacted with an acid (e.g. hydrochloric acid, trifluoroacetic acid, trifluoromethanesulfonic acid, etc.) to give the compound [XXIV]. Besides, when the group $R^9$ is benzyl, the compound [XXIII] is catalytically reduced in the presence of a catalyst (e.g. Pd/C etc.) to give the compound [IId]. The compound [XXIV] wherein $R^7$ is benzyloxy can also be converted into the compound [IId] by removal of the benzyl group in the same manner as described in Process A hereinbefore.

Reaction Scheme-III

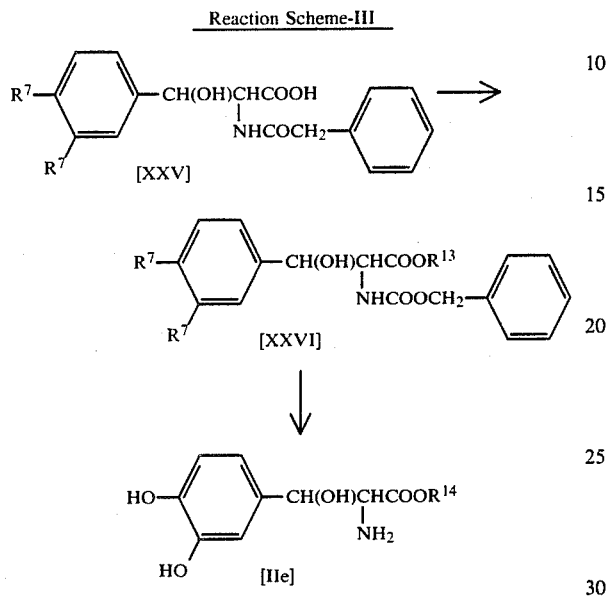

wherein $R^7$ is as defined hereinbefore, and $R^{13}$ is a $C_3$-$C_4$ alkenyl or a $C_5$-$C_6$ cycloalkenyl, and $R^{14}$ is a $C_3$-$C_4$ alkyl or a $C_5$-$C_6$ cycloalkyl.

The compound [XXV] is converted into the compound [XXVI] by reacting the compound [XXV] with a compound of the formula:

$$R^{13}-Hal \qquad [XXX]$$

wherein $R^{13}$ is as defined above, and Hal means a halogen atom such as chlorine, bromine or iodine, in an organic solvent (e.g. dimethylformamide, etc.) in the presence of a condensing agent such as organic bases (e.g. cyclohexylamine, etc.) or inorganic bases (e.g. sodium hydrogen carbonate, etc.). The compound [XXVI] thus obtained is converted into the compound [IIe] by subjecting the compound [XXVI] to catalytic reduction in the same manner as described in Process A hereinbefore.

Other starting compounds [XIX] can be prepared by the process as shown in the following reaction scheme-IV.

Reaction Scheme-IV

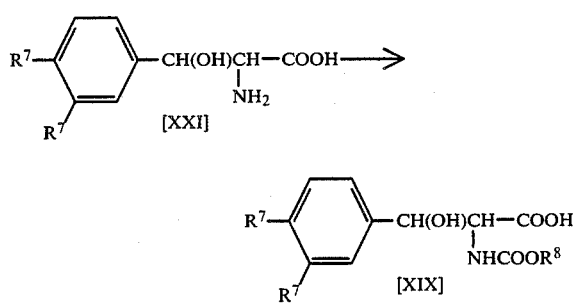

wherein $R^7$ and $R^8$ are as defined hereinbefore.

The compound [XXI] can be converted into the compound [XIX] by reacting the compound [XXI] with ditert-butyl dicarbonate or 2-(tert-butoxycarbonyloxyimino)-2-phenylacetonitrile, etc., or alternatively by subjecting the compound [XXI] to Schotten-Baumann reaction with a chloroformate of the formula:

$$R^8OCOCl \qquad [XXVII]$$

wherein $R^8$ is as defined above.

The compounds of the present invention exhibit inhibiting activity against 5-lipoxygenase which participates in the first stage of biosynthesis of various leucotrienes derived from arachidonic acid, and/or antagonistic activity against SRS-A which is the mixture of the above leucotrienes. These activities of the compounds of the present invention are illustrated by the following experiments.

EXPERIMENT 1

Anti-SRS-A activity:

Anti-SRS-A activity of the drugs (the compounds of the present invention) was assayed by using isolated ileum of guinea pig (weighing 300-400 g, male).

SRS-A sample was prepared as follows.

Male albino guinea-pigs were administered by intraperitoneal and subcutaneous injection of 50 mg ovalbumin emulsified with a half amount of Freund's complete adjuvant every other day (total three times). 4 Weeks after the administration lungs were isolated from guinea-pigs and chopped into small pieces. The tissue was placed in Tyrode solution containing indomethacin (1μg/ml) and incubated at 37° C. for 15 min. The incubated solution was then centrifuged and the supernatant fluid was used for the SRS-A sample.

The anti-SRS-A activity was assayed by Magnus method, i.e. a modified method by Eda et al. [cf. Bulletin of Pharmacology in Japan, 66, 194-213 (1970)] using isolated guinea pig ileum. That is, an isolated ileum of guinea pig was hung within an organ bath which was filled with a Tyrode solution containing mepyramine (0.4 μg/ml) and atropine (0.35,/μg/ml) at 37° C. under aeration. The SRS-A sample was given until reproducible contractions were obtained. A solution of the drug (the compounds of the present inventions was added thereto in the final concentration of $10^{-6}$ g/ml or $10^{-6}$M. After 5 minutes, the SRS-A sample was again acted, and the change of contractile response was measured. Based on the change of contractile response, the anti-SRS-A activity (inhibition rate) was calculated by the following equation:

$$\text{Inhibition rate (\%)} = \frac{a^1 - a^2}{a^1} \times 100$$

wherein $a^1$: Contractile response before administration of a drug.

$a^2$: Contractile response after administration of a drug.

The results are shown in Table 1.

TABLE 1

| Test compound (Compd. No.) | Inhibition (%) | Test compound (Compd. No.) | Inhibition (%) |
|---|---|---|---|
| 10 | 100* | 122 | 94 |
| 13 | 100* | 132 | 82 |

TABLE 1-continued

| Test compound (Compd. No.) | Inhibition (%) | Test compound (Compd. No.) | Inhibition (%) |
|---|---|---|---|
| 19 | 100 | 142 | 91 |
| 28 | 94* | 143 | 83 |
| 29 | 97* | 146 | 94 |
| 34 | 92* | 147 | 100 |
| 35 | 87* | 156 | 90 |
| 41 | 81* | 158 | 96 |
| 42 | 97* | 170 | 85 |
| 48 | 100 | 177 | 86 |
| 65 | 85* | 178 | 81 |
| 77 | 96* | 183 | 97 |
| 120 | 97 | 189 | 98 |

*Inhibition rate (%) at a concentration of a drug of $10^{-6}$ M and others are that at a concentration of a drug of $10^{-6}$ g/ml.

EXPERIMENT 2

5-Lipoxygenase inhibitory activity (Inhibition of 5-HETE production):

The inhibitory activity was assayed in the same manner as described by J. Harvey et al. That is, leucocytes isolated from abdominal cavity of guinea pig were suspended in Krebs Ringer buffer (KRB, pH 7.4) in a concentration of $2.2 \times 10^7$ cells/mg. The leucocytes suspension (935 μl) was preincubated with shaking at 37° C. for 10 minutes, and thereto was added a solution (10 μl) of test drugs (the compounds of the present invention) in dimethylsulfoxide (DMSO) (the final concentration of the compound being 10 μM in the solution). The mixture was incubated for 10 minutes, and then, $^{14}$C-arachidonic acid (0.1 μCi, 50 μl) (in 5% ethanol/KRB) and A 23187 (J. Pharmacol. Methods, 9, 147–155(1983), 5 μg in 5 μl DMSO) were added thereto, and the mixture was further incubated for 10 minutes. Ice-cooled 0.2M aqueous citric acid solution (100 μl) was added thereto in order to stop the reaction, and then, water (4 ml) was further added thereto. The mixture was twice extracted with ethyl acetate (each 2.5 ml), and the organic layer was distilled to dryness under nitrogen. The resulting residue was dissolved in ethyl acetate and the solution was applied onto a TLC plate. After developing with toluene-dioxane-acetic acid (65:34:1.5 V/V), 5-HETE (5-hydroxyeicosatetraenoic acid) produced by 5-lipoxygenase was measured with TLC scanner. The inhibition rate (%) was calculated by comparing the amount of 5-HETE between the addition and non-addition of a drug by the following equation:

$$\text{Inhibition rate (\%)} = \frac{b^1 - b^2}{b^1} \times 100$$

wherein $b^1$: Amount of produced 5-HETE in case of non-addition of a drug.

$b^2$ Amount of produced 5-HETE in case of addition of a drug.

The results are shown in Table 2.

TABLE 2

| Test compound (Compd. No.) | Inhibition (%) | Test compound (Compd. No.) | Inhibition (%) |
|---|---|---|---|
| 19 | >70 | 132 | >70 |
| 77 | >70 | 142 | >70 |
| 122 | >70 | 183 | >70 |

The present invention is illustrated by the following Examples but should not be construed to be limited thereto.

EXAMPLE 1

DL-Threo-3-(3,4-dibenzyloxyphenyl)-N-benzyloxycarbonylserine

To an aqueous tetrahydrofuran solution (H₂O 172 g, THF 151 g) of potassium hydroxide (10 g) is added portionwise DL-threo-3-(3,4-dibenzyloxyphenyl)serine hydrochloride (36 g) at a temperature below 7° C. To the resulting solution is added carbobenzoxy chloride (15.3 g) over 30 min. while maintaining pH 8.5–9.5 with 22% aqueous KOH solution. After 1.5 hr., 10% hydrochloric acid is added to the reaction mixture below 10° C. to adjust pH 6.4–7, and then the solution is condensed to ⅔ of the initial volume under atmospheric pressure. Conc. hydrochloric acid is added to adjust the pH below 0.5 at 40° C. and the resulting mixture stirred for 1 hr. at the same temperature. 22% aqueous KOH solution is added to adjust pH 3 and the precipitate is filtered and washed with water and n-heptane to give the title compound (44.1 g), mp. 139°–140° C. (Compd. No. 1).

Following this procedure, compounds 2 to 4 in Table 3 are obtained.

Compounds 5 to 7 in Table 3 are obtained by the procedure described in Japanese Patent Application "Kokai" (Laid-Open) No. 32540/76.

TABLE 3

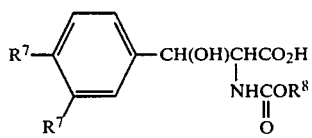

[XIX]

| Compd. No. | R⁷ | R⁸ | | mp. | $[\alpha]_D^{25}$ |
|---|---|---|---|---|---|
| 1 | OCH₂—⟨phenyl⟩ (×2) | CH₂—⟨phenyl⟩ | DL threo | 139–140° C. | — |
| 2 | OCH₂—⟨phenyl⟩ (×2) | CH₂—⟨phenyl⟩ | D threo | 176° C. | +35° (DMF, C = 1.0) |

TABLE 3-continued

[XIX]

$$R^7\text{-}\underset{R^7}{\text{C}_6\text{H}_3}\text{-CH(OH)CHCO}_2\text{H} \atop \underset{\underset{\text{O}}{\|}}{\text{NHCOR}^8}$$

| Compd. No. | $R^7$ | $R^8$ | | mp. | $[\alpha]_D^{25}$ |
|---|---|---|---|---|---|
| 3 | OCH$_2$—C$_6$H$_5$ | CH$_2$—C$_6$H$_5$ | L threo | 176° C. | −35.2° (DMF, C = 1.0) |
| 4 | OCH$_2$—C$_6$H$_5$ | CH$_2$—C$_6$H$_5$ | DL erythro | 139–142° C. | — |
| 5 | OH | CH$_2$—C$_6$H$_5$ | DL threo | 140° C. | — |
| 6 | OH | CH$_2$—C$_6$H$_5$ | D threo | amorphous | +27.1° (MeOH, C = 1.0) |
| 7 | OH | CH$_2$—C$_6$H$_5$ | L threo | amorphous | −27.1° (MeOH, C = 1.0) |

EXAMPLE 2

DL-Threo-3-(3,4-dibenzyloxyphenyl)-N-t-butoxycarbonylserine

To a mixture of DL-threo-3-(3,4-dibenzyloxyphenyl)serine hydrochloride (860 mg), water (10 ml) and tetrahydrofuran (8 ml) is added sodium bicarbonate (353 mg), and the resulting mixture is stirred at room temperature for 2 hr. To this mixture is added a tetrahydrofuran solution (2 ml) of di-t-butyl dicarbonate (480 mg) at 0° C. and the resulting mixture is stirred at the same temperature for 1 hr and at room temperature for 2 hr. Solid citric acid is added to the reaction mixture to adjust pH 3. Addition of water and n-hexane results in precipitation of the title compound (900 mg) (Compd. No. 8) as a white solid. m.p. 108°–110° C.

EXAMPLE 3

L-Threo-3-(3,4-dihydroxyphenyl)-N-(1-methyl-3-phenylpropyl)serine pyrrolidine amide (1) To a solution of L-threo-3-(3,4-dihydroxyphenyl)-N-benzyloxycarborylserine (54 g) and N-methylmorphorine (16.38 g) in dry tetrahydrofuran (600 ml) is added a solution of isobutyl chloroformate (21.85 g) in the same solvent (10 ml) at an inner temperature of −10° to −20° C. After the addition is completed, the reaction mixture is stirred at −5° to −10° C. for 20 min. The inner temperature is again lowered to about −20° C., and then a solution of pyrrolidine (16.32 g) in dry tetrahydrofuran (140 ml) is added to the reaction mixture over 15 min. The reaction mixture is slowly warmed to 0° C. over 1 hr. and stirred overnight at room temperature. After evaporation of the solvent, ethyl acetate and 2% aqueous sodium bicarbonate solution are added to the residue. The organic layer is separated and successively washed with 2% aqueous sodium bicarbonate solution twice, 5% hydrochloric acid twice and brine, dried over anhydrous sodium sulfate and condensed under reduced pressure. The residue is subjected to a silica-gel column-chromatography (eluent; chloroform/methanol/acetic acid = 100/4/4→100/7/5), and crystallized from n-hexane to give pure L-threo-3-(3,4-dihydroxyphenyl)-N-benzyloxycarbonylserine pyrrolidine amide (Compd. No. 9), [33.85 g (54%)], m.p. 116°–118° C. $[\alpha]_D^{25} = +31.3°$ (MeOH, C=1.05).

(2) L-Threo-3-(3,4-dihydroxyphenyl)-N-benzyloxycarbonylserine pyrrolidine amide (12.01 g) is hydrogenolyzed in methanol (350 ml) in the presence of 5% Pd/C (50% moist) (2.0 g) and acetic acid (3.5 ml) at room temperature and ordinary pressure. After the completion of the reaction, the catalyst is removed by filtration and the filtrate is condensed under reduced pressure to give crude L-threo-3-(3,4-dihydroxyphenyl)serine pyrrolidine amide as an amorphous solid, which is used for the next reaction without any purification.

(3) Crude L-threo-3-(3,4-dihydroxyphenyl)serine pyrrolidine amide is dissolved in dry methanol (350 ml). To this solution are added molecular sieves 3A (15 g), acetic acid (3.5 ml) and benzylacetone (6.8 ml), and the reaction mixture is cooled in an ice water bath. Sodium cyanoborohydride (3.97 g) is added to the reaction mixture, and the mixture is stirred under ice-cooling for 1 hr. and at room temperature for 2 days. Insoluble materials are filtered off and the filtrate is condensed.

The resulting residue is dissolved in ethyl acetate, which is washed successively with 2% aqueous sodium bicarbonate solution twice and brine. This ethyl acetate layer is condensed under reduced pressure and the residue is dissolved in 5% hydrochloric acid and the aqueous layer is washed with ether to remove non-amine materials. The aqueous solution is made alkaline with solid sodium bicarbonate, and the liberated amine is extracted with ethyl acetate. The extract is washed with brine twice, dried over anhydrous sodium sulfate and evaporated to give the title compound (Compd. No. 10) as an amorphous solid. Addition of ethereal hydrogen chloride to the dichloromethane sclution of this free base affords hydrochloride salt as a white solid (11.95 g). m.p. 129°–131° C. $[\alpha]_D^{25} = +22.5°$ (MeOH, C=1.0).

EXAMPLE 4

DL-Threo-3-(3,4-dihydroxyphenyl)-N-(1-methyl-3-phenylpropyl)serine piperidine amide (1) To a solution of DL-threo-3-(3,4-dibenzyloxyphenyl)-N-benzyloxycarbonylserine (10.55 g) and N-methylmorphorine (2.05 g) in dry tetrahydrofuran (80 ml) is added isobutyl chloroformate (2.91 g) under the same conditions as described in Example 3-(1). The resulting mixed anhydride is treated with a solution of piperidine (3.37 g) in dry tetrahydrofuran (20 ml). After removal of the solvent under reduced pressure, the resulting mixture is partitioned between water and benzene-ethyl acetate mixture. The organic layer is dried over anhydrous sodium sulfate and condensed under reduced pressure. The residue is subjected to a solicagel column chromatography (eluent; chloroform/acetone=15/1) to give DL-threo-3-(3,4-dibenzyloxyphenyl)-N-benzyloxycarbonylserine piperidine amide (Compd. No. 11) (5.85 g). m.p. 125°–126° C.

(2) DL-threo-3-(3,4-dibenzyloxyphenyl)-N-benzyloxycarbonylserine piperidine amide (4.17 g) is hydrogenolyzed in a THF (60 ml)—MeOH (60 ml) mixture in the presence of 5% Pd/C (50% moist) (0.7 g) and acetic acid (0.8 ml) at ordinary temperature and pressure. After the reaction is completed, the catalyst is removed by filtration and the filtrate is condensed to give crude 3-(3,4-dihydroxyphenyl)serine piperidine amide, which is used in the next reaction without any purification.

(3) The reductive alkylation of 3-(3,4-dihydroxyphenyl)serine piperidine amide with benzylacetone is carried out as is described in Example 3-(3). The title compound is obtained as hydrochloride (Compd. No. 12) (1.88 g). m.p. 125°–128° C.

Following the procedures described in Examples 3 and 4, compounds shown in Table 4 are obtained. The intermediary N-protected phenylserine amides obtained by the procedures in Example 3 and 4 are summarized in Table 5 and 6, respectively.

TABLE 4

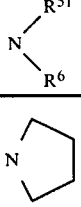

| Compd. No. | | | $\begin{array}{c}\phantom{x}R^{51}\\N\\\phantom{x}R^6\end{array}$ | NHR | m.p. (HCl salt) | $[\alpha]_D^{25}$ (HCl salt, MeOH/C = 1.0) |
|---|---|---|---|---|---|---|
| 13 | DL | threo | 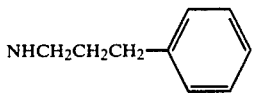 | NHCH₂CH₂CH₂— 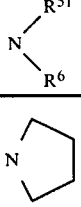 | 120–128° C. | — |
| 14 | L | " | " | " | 120–122° C. | +14.6° |
| 15 | D | " | " | " | 128–130° C. | −15.4° |
| 16 | DL | erythro | " | " | 88–97° C. | — |
| 17 | L | threo | " | NHCH₂CH₂CH— 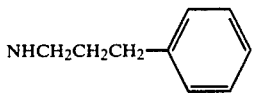 <br>               CH₃ | 135–137° C. | +17.4° |
| 18 | L | " | " | NHCH₂— 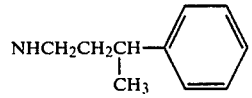 | 130–132° C. (base) | +22.1° |
| 19 | DL | " | " | NHCHCH₂CH₂— 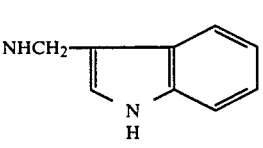 <br>     CH₃ | 114–120° C. | — |
| 10 | L | " | " | " | 129–131° C. | +22.5° |
| 20 | D | " | " | " | 125–128° C. | −20.7° |
| 21 | DL | erythro | " | " | 75–80° C. | — |

TABLE 4-continued $$\underset{\underset{HO}{HO}}{\text{HO}}\text{—}CH(OH)CHCON\underset{R^6}{\overset{R^{51}}{\diagdown}}$$
$$\phantom{xxxxxxxxxxxxxxxxxx}\underset{NHR}{|}$$

| Compd. No. | | | $\underset{R^6}{\overset{R^{51}}{\diagup}}N\diagdown$ | NHR | m.p. (HCl salt) | $[\alpha]_D^{25}$ (HCl salt, MeOH/C = 1.0) |
|---|---|---|---|---|---|---|
| 22 | L | threo | " | NHCHCH$_2$CH$_2$—cyclohexyl, CH$_3$ | 125–127° C. | +7.9° |
| 23 | L | " | " | NHCHCH$_2$CH$_2$CH(CH$_3$)$_2$, CH$_3$ | 133–135° C. | +7.3° |
| 24 | L | " | " | NHCHCH$_2$CH$_2$—C$_6$H$_4$—CH(CH$_3$)$_2$, CH$_3$ | 115–120° C. | +23.3° |
| 25 | L | " | " | NHCHCH$_2$CH$_2$—C$_6$H$_4$—OH, CH$_3$ | 123–130° C. | +27.4° |
| 26 | L | " | " | NHCHCH$_2$CH$_2$—C$_6$H$_4$—OCH$_3$, CH$_3$ | 145–147° C. | +27.4° |
| 27 | L | " | " | NHCHCH$_2$CH$_2$—C$_6$H$_4$(o-OCH$_3$), CH$_3$ | 134–136° C. | +13.9° |
| 28 | L | " | " | NHCHCH$_2$CH$_2$—C$_6$H(CH$_3$)$_3$—OCH$_3$, CH$_3$ | 168–170° C. | +3.9° |
| 29 | L | " | " | NHCHCH$_2$CH$_2$—C$_6$H$_4$—F, CH$_3$ | 135–138° C. | +18.5° |
| 30 | L | " | " | NHCHCH$_2$CH$_2$—C$_6$H$_4$(o-Cl), CH$_3$ | 121–124° C. | +7.2° |
| 31 | L | " | " | NHCHCH$_2$CH$_2$—C$_6$H$_4$(m-CF$_3$), CH$_3$ | 139–141° C. | +15.8° |

TABLE 4-continued $$\text{HO}-\underset{\text{HO}}{\bigcirc}-\text{CH(OH)CHCON}\underset{R^6}{\overset{R^{51}}{\diagdown}}$$
$$\underset{\text{NHR}}{|}$$

| Compd. No. | | $\underset{R^6}{\overset{R^{51}}{\diagdown}}N\diagup$ | NHR | m.p. (HCl salt) | $[\alpha]_D^{25}$ (HCl salt, MeOH/C = 1.0) |
|---|---|---|---|---|---|
| 32 | L | " | " NHCHCH₂CH₂–⟨C₆H₄⟩–N(CH₃)₂ <br>     CH₃ | 184–187° C. (2HCl) | +14.1° |
| 33 | L | " | " NHCHCH₂CH₂–⟨C₆H₃⟩(O,O-ethylenedioxy) <br>     CH₃ | 130–132° C. | +23.4° |
| 34 | L | " | " NHCHCH₂CH₂–(naphthyl) <br>     CH₃ | 155–158° C. | +3.2° |
| 35 | L | " | " NHCHCH₂CH₂–(furyl) <br>     CH₃ | 124–127° C. | +19.7° |
| 36 | L | " | " NHCHCH₂CH₂–(pyrrolyl-NH) <br>     CH₃ | 133–135° C. (base) | +16.3° |
| 37 | L | " | " NHCHCH₂CH₂–⟨C₆H₅⟩ <br>     CH₂CH₃ | 118–120° C. | +10.0° |
| 38 | L | " | " NHCH(CH₂)₃–⟨C₆H₅⟩ <br>     CH₃ | 128–130° C. | +17.2° |
| 39 | L | " | " NHCH(CH₂)₄–⟨C₆H₅⟩ <br>     CH₃ | 142–144° C. | +11.0° |
| 40 | DL | " | " NHCH(CH₂)₄CNH–⟨C₆H₄⟩–C₄H₉(n) <br>     CH₃    ‖<br>            O | 145–152° C. | — |
| 41 | L | " | " " | 142–150° C. | +7.1° |
| 42 | L | " | " NHCH(CH₂)₄CNH–⟨C₆H₄⟩–CF₃ <br>     CH₃    ‖<br>            O | 170–172° C. | +6.5° |

TABLE 4-continued $$\text{HO-C}_6\text{H}_3(\text{OH})\text{-CH(OH)CHCON}(R^{51})(R^6),\ \text{NHR}$$

| Compd. No. | | $N(R^{51})(R^6)$ | NHR | m.p. (HCl salt) | $[\alpha]_D^{25}$ (HCl salt, MeOH/C = 1.0) |
|---|---|---|---|---|---|
| 43 | L | " | NHCH(CH₃)CH₂O-C₆H₅ | 145–150° C. | +12.0° |
| 44 | L | " | NHCH(CH₃)CH₂O-C₆H₄(OCH₃) | 125–127° C. | −10.5° |
| 45 | L | " | NHCH(CH₃)CH₂N(CH₃)-C₆H₅ | 164–166° C. (2HCl) | +21.6° |
| 46 | L | " | NHCH(CH₃)CH₂-O-benzodioxane | 163–165° C. | +15.5° |
| 47 | L | " | NH-tetralin-2-yl | 157–160° C. | −6.7° |
| 48 | DL | " | NHCH₃ | NHCH(CH₃)CH₂C₆H₅ | 125–128° C. | — |
| 49 | DL | " | NHCH₂CH₃ | " | 120–124° C. | — |
| 50 | DL | " | NH(CH₂)₃CH₃ | " | 120–124° C. | — |
| 51 | DL | " | NHCH₂CH₂OH | " | 140–150° C. | — |
| 52 | DL | " | NHCH₂CH₂OCH₃ | " | 103–108° C. | — |
| 53 | DL | " | NHCH₂CH₂N(CH₃)₂ | " | 120–130° C. (fumarate) | — |
| 54 | DL | " | NH-cyclopentyl | " | 135–138° C. | — |
| 55 | DL | " | NH-C₆H₅ | " | 135–142° C. | — |
| 56 | DL | " | NH-pyridin-3-yl | " | 162–168° C. (2HCl) | — |

TABLE 4-continued $$\underset{HO}{\overset{HO}{\bigcirc}}-CH(OH)CHCON\overset{R^{51}}{\underset{R^6}{\diagdown}}$$

| Compd. No. | | $N\overset{R^{51}}{\underset{R^6}{\diagdown}}$ | NHR | m.p. (HCl salt) | $[\alpha]_D^{25}$ (HCl salt, MeOH/C = 1.0) |
|---|---|---|---|---|---|
| 57 | DL | " 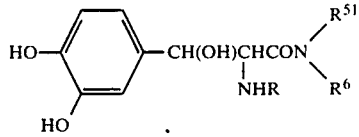 NH—C₆H₄—CO₂H | " | 125–130° C. | — |
| 58 | DL | " 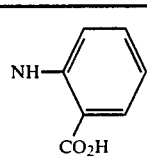 NH—C₆H₄—CO₂CH₃ | " | 114–118° C. | — |
| 59 | DL | " 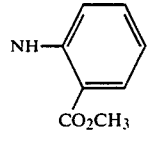 NH-tetrazole | " | 130–140° C. | — |
| 60 | DL | " N(CH₃)₂ | " | 125–130° C. | — |
| 61 | DL | " N(C₂H₅)₂ | " | 101–113° C. | — |
| 12 | DL | " 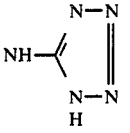 piperidine | " | 125–128° C. | — |
| 62 | DL | " 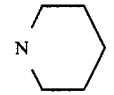 azepane | " | 117–119° C. | — |
| 63 | DL | " 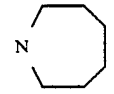 morpholine | " | 138–148° C. | — |
| 64 | DL | " NHNHCOCH₃ | " | 173–176° C. | — |
| 65 | L | " 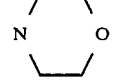 proline-CO₂CH₃ | " | 124–127° C. | −40.8° |
| 66 | L | " 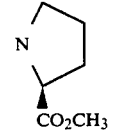 proline-CO₂H | " | 158–160° C. | −45.2° |
| 67 | L | "  prolinol-CH₂OH | " | 130–133° C. | −1.4° |

TABLE 4-continued

Structure: HO, HO-C6H3-CH(OH)CH(NHR)CON(R51)(R6)

| Compd. No. | | | NR51R6 | NHR | m.p. (HCl salt) | $[\alpha]_D^{25}$ (HCl salt, MeOH/C = 1.0) |
|---|---|---|---|---|---|---|
| 68 | DL | " | 2,5-dimethylpyrrolidin-1-yl | " | 135–138° C. | — |
| 69 | L | " | 2-methylpyrrolidin-1-yl | " | 72–76° C. | +19.1° |
| 70 | DL | " | azetidin-1-yl | " | 133–135° C. | — |
| 71 | L | " | 4-methylpiperidin-1-yl | " | 80–85° C. | −6.8° |
| 72 | L | " | 4-phenylpiperidin-1-yl | " | 110–120° C. | +14.8° |
| 73 | DL | " | 3-azabicyclo[3.2.2]nonan-3-yl | " | 133–136° C. | — |
| 74 | DL | " | 4-methylpiperazin-1-yl | " | 148–150° C. (fumarate) | — |
| 75 | DL | " | 4-phenylpiperazin-1-yl | " | 180–183° C. (2HCl) | — |
| 76 | L | " | N-ethylanilino | " | 58–65° C. | −6.3° |
| 77 | DL | " | indolin-1-yl | " | 150–153° C. | — |

TABLE 4-continued $$HO-\text{(3,4-dihydroxyphenyl)}-CH(OH)CHCON\begin{smallmatrix}R^{51}\\R^6\end{smallmatrix}$$
$$|\\NHR$$

| Compd. No. | | N⟨R^51/R^6 | NHR | m.p. (HCl salt) | $[\alpha]_D^{25}$ (HCl salt, MeOH/C = 1.0) |
|---|---|---|---|---|---|
| 78 | L | " (octahydroindole) | " | 88–97° C. | +18.8° |
| 79 | L | " (1,2,3,4-tetrahydroisoquinoline) | " | 95–102° C. | −16.0° |
| 80 | L | " (isoindoline) | " | 159–161° C. | +13.2° |

TABLE 5

$$HO-\text{(3,4-dihydroxyphenyl)}-CH(OH)CHCON\begin{smallmatrix}R^{51}\\R^6\end{smallmatrix}$$
$$|\\NHCOOCH_2C_6H_5$$

| Compd. No. | | | N⟨R^51/R^6 | m.p. | $[\alpha]_D^{25}$ (MeOH/C = 1.0) |
|---|---|---|---|---|---|
| 81 | DL | threo | (pyrrolidine) | 115–117° C. | — |
| 9 | L | " | " | 116–118° C. | +31.3° |
| 82 | D | " | " | 112–116° C. | −29.5° |
| 83 | DL | erythro | " | 62–64° C. | — |
| 84 | L | threo | (2-CO₂CH₃-pyrrolidine) | 132–135° C. | −40.9° |
| 85 | L | " | (2-CO₂CH₂C₆H₅-pyrrolidine) | 93–95° C. | −40.7° |
| 86 | L | " | (2-CH₂OH-pyrrolidine) | 154–156° C. | +6.4° |

TABLE 5-continued $$\text{HO} \diagdown \text{C}_6\text{H}_3(\text{OH}) - \text{CH(OH)CHCON} \diagup {R^{51} \atop R^6}$$
$$\text{NHCOOCH}_2\text{C}_6\text{H}_5$$

| Compd. No. | | | N(R⁵¹)(R⁶) | m.p. | $[\alpha]_D^{25}$ (MeOH/C = 1.0) |
|---|---|---|---|---|---|
| 87 | DL | " | 2,6-dimethylpiperidine | 107–110° C. | — |
| 88 | L | " | 2-methylpyrrolidine | low m.p. | +17.4° |
| 89 | DL | " | azetidine | 110–113° C. | — |
| 90 | L | " | 4-methylpiperidine | 53–58° C. | −5.9° |
| 91 | L | " | 4-phenylpiperidine | 56–63° C. | +2.3° |
| 92 | DL | " | 3-azabicyclo[3.2.2] | 96–99° C. | — |
| 93 | DL | " | 4-methylpiperazine | 135–140° C. | — |
| 94 | DL | " | 4-phenylpiperazine | 118–120° C. | — |
| 95 | DL | " | indoline | 217–219° C. | — |
| 96 | L | " | 1,2,3,4-tetrahydroisoquinoline | 62–67° C. | +1.7° |

TABLE 5-continued

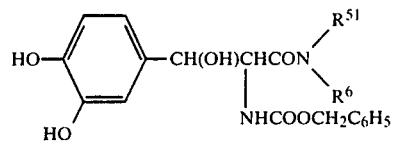

| Compd. No. | | | | m.p. | $[\alpha]_D^{25}$ (MeOH/C = 1.0) |
|---|---|---|---|---|---|
| 97 | L | " | 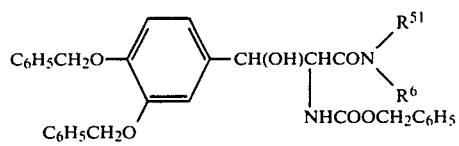 | 123–125° C. | +39.7° |

TABLE 6

| Compd. No. | | | R⁶ | m.p. |
|---|---|---|---|---|
| 98 | DL | threo | NHCH₃ | 165–167° C. |
| 99 | " | " | NHCH₂CH₂ | 185–187° C. |
| 100 | " | " | NH(CH₂)₃CH₃ | 168–169° C. |
| 101 | " | " | NH-CH₂CH₂-OH | 77–80° C. |
| 102 | " | " | NH-CH₂CH₂-OCH₃ | 155–157° C. |
| 103 | " | " | NH-CH₂CH₂-N(CH₃)₂ | 140–141.5° C. |
| 104 | " | " | NH-cyclopentyl | 180–184° C. |
| 105 | " | " | NH-phenyl | 193–195° C. |
| 106 | " | " | NH-(3-pyridyl) | 76–78° C. |
| 107 | " | " | NH-(2-COOH-phenyl) | 192–194° C. |
| 108 | " | " | NH-(2-CO₂CH₃-phenyl) | 140–142° C. |

TABLE 6-continued

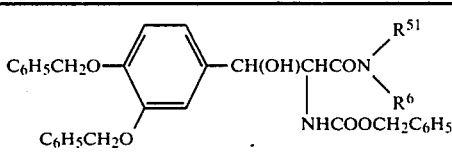

| Compd. No. | | | R⁶ | m.p. |
|---|---|---|---|---|
| 109 | " | " | NH-C(=N-N)NH (tetrazolyl) | 214–218° C. |
| 110 | " | " | N(CH₃)₂ | 75–78° C. |
| 111 | " | " | N(C₂H₅)₂ | low m.p.* |
| 112 | " | " | N-pyrrolidinyl | 118–120° C. |
| 11 | " | " | N-piperidinyl | 125–126° C. |
| 113 | " | " | N-hexamethyleneimino | 124–126° C. |
| 114 | " | " | N-morpholino | 120–122° C. |
| 115 | " | " | NHNHCOCH₃ | 223–225° C. |

*NMR δ$_{CDCl_3}^{TMS}$ (ppm): 0.99(t, 6H), 2.9–3.5(m, 4H), 3.89(br, 1H), 4.61(dd, 1H), 4.89(d, 1H), 4.99 & 5.11(s, 2H+4H), 5.88(d, 1H), 6.85 & 7.09(s, 2H+H), 7.25–7.5(m, 15H)

EXAMPLE 5

DL-Threo-3-(3,4-dihydroxyphenyl)-N-(1-methyl-3-phenylpropyl)serine methyl ester (1) DL-Threo-3-(3,4-dibenzyloxyphenyl)serine hydrochloride (200 g) is dissolved in methanol (980 ml) and the solution is cooled to −10° to 0° C., and thereto is added dropwise thionyl chloride (98 ml) at 0° to −10° C. After the addition, the mixture is stirred at 40° to 50° C. for 4 hours, and thereafter, the reaction mixture is distilled under reduced pressure to remove methanol. To the residue is added isopropyl alcohol, and the mixture is again distilled under reduced pressure. This procedure is repeated three times. To the residue is added isopropyl alcohol, and the precipitate is separated by filtration to give threo-3-(3,4-dibenzyloxyphenyl)serine methyl ester hydrochloride (135.3 g), m.p. 150°–151° C. (Compd. No. 116).

(2) Compound No. 116 obtained above (62.2 g) and benzylacetone (26.9 g) are added to methanol (780 ml), and the mixture is cooled to 0° to 5° C., and thereto is added sodium cyanoborohydride (20.2 g) at 0° to 5° C. The mixture is stirred at room temperature overnight and then distilled under reduced pressure to remove methanol. To the residue is added aqueous sodium hydrogen carbonate, and the mixture is extracted with ethyl acetate. The ettyl acetate layer is washed with saturated aqueous sodium chloride, dried over magnesium sulfate, and distilled to remove ethyl acetate. The residue is purified by silica gel column chromatography and then crystallized from isopropyl alcohol to separate two diastereomers to give DL-threo-3-(3,4-dibenzyloxyphenyl)-N-(1-methyl-3-phenylpropyl)serine methyl ester (diastereomers-I and -II).

Diastereomer-I (Compd. No. 117); yield: 29.7 g, m.p. 88°–90° C.

Diastereomer-II (Compd. No. 118); yield: 28.2 g, IR γ (film) cm$^{-1}$: 1740, 1600, 1505, 1450, 1380, 1265, 1160, 1130, 1020.

(3) Compound No. 117 obtained above (3.78 g) is dissolved in methanol (150 ml) and thereto is added 5% Pd/C (50% moist) (0.75 g), and the mixture is subjected to catalytic reduction under hydrogen. After confirming the stop of absorption of hydrogen, Pd/C is removed by filtration, and the reaction mixture is distilled under reduced pressure to remove methanol. To the residue is added isopropyl alcohol, and the precipitate is separated by filtration. The crystal is re-crystallized from isopropyl alcohol to give DL-threo-3-(3,4-dihydroxyphenyl)-N-(1-methyl-3-phenylpropyl)serine methyl ester (diastereomer-I) (1.44 g), m.p. 120.5°–121.5° C. (Compd. No. 119).

(4) Compound No. 118 obtained above (3.97 g) is treated in the same manner as described in the above (3) to give oily DL-threo-3-(3,4-dihydroxyphenyl)-N-(1-methyl-3-phenylpropyl)serine methyl ester (diastereomer-II) (1.99 g) (Compd. No. 120).

IR γ (film) cm$^{-1}$: 3600–2200 (broad), 1740, 1600, 1460, 1380, 1300, 1260, 1200.

(5) DL-Threo-3-(3,4-dibenzyloxyphenyl)serine methyl ester obtained in the above Example 5-(1) is reacted with 4-p-methoxyphenyl-2-butanone in the same manner as described in the above (2), and the resulting compound is crystallized from cyclohexane. The crystal thus obtained is recrystallized from diisopropyl ether/cyclohexane (⅔) give DL-threo-3-(3,4-dibenzyloxyphenyl)-N-[1-methyl-3-(p-methoxyphenyl)-propyl]serine methyl ester (diastereomerically single) (Compd. No. 121), m.p. 83°–85° C.

Besides, the atove compound is treated in the same manner as described in the above (3) to give DL-threo-3-(3,4-dihydroxyphenyl)-N-[1-methyl-3-(p-methoxyphenyl)propyl]serine methyl ester (Compd. No. 122), m.p. 76°–78° C.

(6) The above (2) is repeated except that acetophenone is used instead of benzylacetone and the reaction product is separated by preparative silica gel thin layer chromatography (developing solvent; chloroform/methanol = 100/1) to give two diastereomers of DL-threo-3-(3,4-dibenzyloxyphenyl)-N-(1-phenethyl)serine methyl ester. One diastereomer having a lower polarity is treated in the same manner as described in the above (3) to give one diastereomer of DL-threo-3-(3,4-dihydroxyphenyl)-N-(1-phenethyl)serine methyl ester (Compd. No. 123), m.p. 84° C. Besides, another diastereomer having a higher polarity is treated likewise to give another diastereomer of DL-threo-3-(3,4-dihydroxyphenyl)-N-(1-phenethyl)serine methyl ester (Compd. No. 124), m.p. 65° C.

(7) The above (2) is repeated except that phenoxyacetone is used instead of benzylacetone and the reaction product is separated by silica gel column chromatography to give two diastereomers of DL-threo-3-(3,4-dibenzyloxyphenyl)-N-(1-methyl-2-phenoxyethyl)serine methyl ester. One diastereomer having a lower polarity (Rf=0.3, benzene/ethyl acetate=15/1) is treated in the same manner as described in the above (3) to give one diastereomer of DL-threo-3-(3,4-dihydroxyphenyl)-N-(1-methyl-2-phenoxyethyl)serine methyl ester (Compd. No. 125), m.p. 89°–93° C. (in acetic acid salt thereof). Besides, another diastereomer having a higher polarity (Rf=0.2) is treated likewise to give another diastereomer of DL-threo-3-(3,4-dihydroxyphenyl)-N-(1-methyl-2-phenoxyethyl)serine methyl ester (Compd. No. 126), m.p. 70°–73° C. (in acetic acid salt).

(8) DL-Erythro-3-(3,4-dibenzyloxyphenyl)serine methyl ester hydrochloride (m.p. 143°–145° C., Compd. No. 127) prepared in the the same manner as described in the above Example 5-(1) is reacted with benzylacetone in the same manner as described in the above (2), and the resulting crystal thus obtained is recrystallized from isopropyl alcohol to give DL-erythro-3-(3,4-dibenzyloxyphenyl)-N-(1-methyl-3-phenylpropyl)serine methyl ester (diastereomerically single) (Compd. No. 128), m.p. 121°–124° C.

Besides, the above compound is treated in the same manner as described in the above (3) to give DL-erythro-3-(3,4-dihydroxyphenyl)-N-(1-methyl-3-phenylpropyl)serine methyl ester (Compd. No. 129), m.p. 121°–123° C.

EXAMPLE 6

DL-Threo-3-(3,4-dihydroxyphenyl)-N-(1-methyl-3-phenylpropyl)serine ethyl ester

DL-Threo-3-(3,4-dibenzyloxyphenyl)serine hydrochloride (4.3 g) and p-toluenesulfonyl cloride (2.88 g) are dissolved in ethanol (30 ml), and the mixture is heated at 45° C. for 2 hours and further refluxed gently for 4 hours. After concentration, to the reaction mixture is added 5% aqueous sodium carbonate, and the organic material is extracted with ethyl acetate. The organic layer is washed with 5% aqueous sodium carbonate and further with saturated aqueous sodium chloride, dried and then filtered. To the filtrate is added a solution of oxalic acid (0.68 g) in ethyl acetate (20 ml). The precipitate is separated by filtration to give DL-threo-3-(3,4-dibenzyloxyphenyl)serine ethyl ester oxalate (Compd. No. 130) (3.1 g), m.p. 128.5°–129.5° C.

The oxalate (3.04 g) obtained above is added to ethanol (55 ml), and thereto are added benzylacetone (1.36 g), molecular sieves 3A (3.5 g) and further sodium cyanoborohydride (0.45 g), and the mixture is stirred at room temperature for 20 hours. The reaction mixture is filtered through celite, and the filtrate is concentrated. To the residue are added 5% aqueous sodium carbonate, and the organic material is extracted with ethyl acetate. The organic layer is washed with 5% aqueous sodium carbonate and saturated aqueous sodium chloride, dried and then concentrated. The residue is purified by silica gel flash column chromatography (eluting solvent, hexane/acetone=4/1) and crystallized from cyclohexane, by which only one of the diastereomers is selectively crystallized, to give DL-threo-3-(3,4-dibenzyloxyphenyl)-N-(1-methyl-3-phenylpropyl)serine ethyl ester (diastereomerically single) (Compd. No. 131) (0.49 g), m.p. 63.5° C.

The ethyl ester (0.48 g) obtained above is dissolved in methanol (30 ml) and hydrogenolyzed in the presence of 10% Pd/C catalyst (57% moist) (0.1 g) under atmospheric pressure for 1 hour. After removal of the catalyst, the reaction mixture is concentrated, and the residue is crystallized from methylene chloride to give the title compound (Compd. No. 132) (0.25 g), m.p. 48° C.

EXAMPLE 7

DL-Threo-3-(3,4-dihydroxyphenyl)-N-[1-methyl-2-(p-methoxyphenyl)ethyl]serine methyl ester DL-Threo-3-(3,4-dibenzyloxyphenyl)serine methyl ester hydrochloride (2.22 g) and 1-(p-methoxyphenyl)-2-propanone (1.00 g) are dissolved in methanol (25 ml), and thereto are added molecular sieves 3A (1.5 g) and further sodium cyanoborohydride (0.33 g), and the mixture is stirred at room temperature overnight. The reaction mixture is filtered through celite, and the filtrate is concentrated under reduced pressure. To the residue is added 5% aqueous sodium carbonate, and the organic material is extracted with ethyl acetate. The orgarnic layer is washed with saturated aqueous sodium chloride, dried over anhydrous sodium sulfate and then concentrated under reduced pressure. The resulting crude product is purified by silica gel flash column chromatography (eluting solvent, n-hexane/acetone=8/5) to give oily DL-threo-3-(3,4-dibenzyloxyphenyl)-N-[1-methyl-2-(p-methoxyphenyl)ethyl]serine methyl ester (Rf=0.8, chloroform/methanol: 97/3).

The compound obtained above (whole amount) is dissolved in methanol (30 ml) and hydrogenolyzed in the presence of 5% Pd/C catalyst (53% moist) (0.2 g) under atmospheric pressure. After the reaction is completed (about 5 hours), the catalyst is removed by filtration, and then the reaction mixture is concentrated, and the residue is purified by silica gel flash column chromatography (eluting solvent, n-hexane/acetone=4/3) and crystallized from methylene chloride to give a diastereomeric mixture of the title compound (Compd. No. 133) (1.18 g), m.p. 93°–95° C.

In the same manner as described in Example 7, DL-threo-3-(3,4-dibenzyloxyphenyl)serine methyl ester hydrochloride is reacted with diverse carbonyl compounds, and the products thus obtained are summarized in Table 7.

TABLE 7

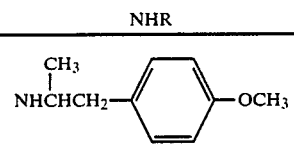

| Compd. No. | R⁷ | | NHR | m.p. |
|---|---|---|---|---|
| 133 | DL threo | OH | NHCHCH₂-⟨C₆H₄⟩-OCH₃ (CH₃) | 93–95° C. |
| 134 | " erythro | OCH₂-⟨C₆H₅⟩ | NHCH₂CH₂CH₂CH₃ | 86–90° C. |
| 135 | " " | OH | " | 110–112° C. |
| 136 | " threo | OH | NHCH₂-(ferrocenyl) | 57.5–58.5° C. |
| 137 | " " | OH | NHCH₂-⟨C₆H₄⟩-F | 87° C. |

TABLE 7-continued

R⁷—[phenyl with R⁷]—CH(OH)CH(NHR)COCH₃

| Compd. No. | R⁷ | | NHR | m.p. |
|---|---|---|---|---|
| 138 | " | " | OH, NHCH₂—C₆H₅ | oil* |
| 139 | " | " | OH, NHCH₂CH₂—C₆H₅ | 78–83° C. |
| 140 | " | " | OH, NHCH₂CH(C₆H₅)₂ | 48–53° C. |
| 141 | " | " | OH, NHCH₂-(indol-3-yl) | 77–80° C. |
| 142 | " | " | OH, NHCH(CH₃)CH₂CH₂CH(CH₃)₂ | 98.5° C. |
| 143 | " | " | OH, NHCH(CH₃)CH₂CH₂—C₆H₄—OH (p) | 70–73° C. |
| 144 | " | " | OH, NH-(1,2,3,4-tetrahydronaphth-2-yl) | 64.5–65.5° C. |
| 145 | " | " | OH, NHCH((CH₂)₃C₆H₅)(C₆H₅) | 80–83° C. (HCl salt) |
| 146 | " | " | OH, NHCH(CH₃)(CH₂)₄C(O)NH—C₆H₄—CF₃ (p) | 104–106° C. |
| 147 | " | " | OH, NHCH(CH₃)(CH₂)₄C(O)NH—C₆H₄—(CH₂)₃CH₃ (p) | 130–134° C. |

TABLE 7-continued

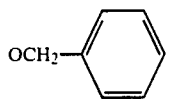

| Compd. No. | R⁷ | | NHR | m.p. |
|---|---|---|---|---|
| 148 | " | " (OCH₂-phenyl) | NHCH(CH₃)₂ | 147–149° C. (HCl salt) |
| 149 | " | " OH | " | 167–169° C. (HCl salt) |
| 150 | " | erythro (OCH₂-phenyl) | NHCH(CH₃)₂ | 144–147° C. (HCl salt) |
| 151 | " | " OH | NHCH(CH₃)₂ | 172–174° C. (HCl salt) |

*IRν(neat)cm⁻¹: 3700–2700, 2950, 1743, 1605, 1455, 1375, 1325, 1285, 1115 and 1020

EXAMPLE 8

L- and D-Threo-3-(3,4-dihyroxyphenyl)-N-(1-methyl-3-phenylpropyl)serine methyl esters (1) L-Threo-3-(3,4-dibenzyloxyphenyl)-N-benzyloxycarbonylserine (5 g) is dissolved in ethyl acetate (50 ml), and thereto is added a diazomethane-ether solution which is prepared from nitrosomethylurea (8 g) and 50% aqueous potassium hydroxide. When yellow color of the solution disappears, the mixture is distilled to remove the solvent, and the residue is dissolved in ethyl acetate. The solution is washed with 1N hydrochloric acid, saturated aqueous sodium hydrogen carbonate and saturated aqueous sodium chloride, and dried over magnesium sulfate, and then ethyl acetate is distilled off under reduced pressure to give L-threo-3-(3,4-dibenzyloxyphenyl)-N-benzyloxycarbonylserine methyl ester (Compd. No. 152) (4.5 g), m.p. 93°–104° C.

(2) The compound No. 152 obtained above (4.5 g) is dissolved in methanol (130 ml), and thereto are added conc. hydrochloric acid (0.9 g) and 5% Pd/C (0.8 g, 50% moist). The mixture is subjected to hydrogenolysis under hydrogen. After confirming the stop of absorption of hydrogen, Pd/C is filtered off. The filtrate is concentrated under reduced pressure, and to the residue is added isopropyl alcohol to give L-threo-3-(3,4-dihydroxyphenyl)serine methyl ester hydrochloride (Compd. No. 153) (1.18 g), m.p. 156° C., $[\alpha]_D^{25}$ −6.8° (c=1, methanol).

(3) The compound No. 153 obtained above (1.0 g) and benzylacetone (0.79 g) are added to methanol (15 ml), and the mixture is cooled to 0° to 5° C. To the mixture is added sodium cyanoborohydride (0.64 g) at 0° to 5° C., and the mixture is stirred at room temperature overnight. Methanol is distilled off under reduced pressure, and to the residue is added saturated aqueous sodium hydrogen carbonate, and then the mixture is extracted with ethyl acetate. The ethyl acetate layer is washed with saturated aqueous sodium chloride, dried over magnesium sulfate, and distilled to remove ethyl acetate. The residue is puified by silica gel chromatography with 2% methanol/chloroform and then crystallized from isopropyl ether to give a mixture of diastereomers of L-threo-3-(3,4-dihydroxphenyl)-N-(1-methyl-3-phenylpropyl)serine methyl ester (Compd. No. 154) (0.53 g), m.p. 79°–81° C., $[\alpha]_D^{25}$ −2.8° (c=1, methanol).

(4) In the same manner as described in the above (1) except that D-threo-3-(3,4-dibenzyloxyphenyl)-N-benzyloxycarbonylserine is used instead of L-threo-3-(3,4-dibenzyloxyphenyl)-N-benzyloxycarbonylserine, there is obtained D-threo-3-(3,4-dibenzyloxyphenyl)-N-benzyloxycarbonylserine methyl ester (Compd. No. 155), m.p. 102°–106° C.

(5) The compound No. 155 is subjected to the debenzylation reaction and subsequent reductive alkylation with benzylacetone in the same manner as described in the above (2) and (3) to give D-threo-3-(3,4-dihydroxyphenyl)-N-( 1-methyl-3-phenylpropyl)serine methyl ester (Compd. No. 156), m.p. 78°–83° C., $[\alpha]_D^{25}$ +1.1° (c=1, methanol).

EXAMPLE 9

DL-Threo-3-(3,4-dihydroxyphenyl)-N-(1-methyl-3-phenylpropyl)serine isopropyl ester and DL-Threo-3-(3,4-dihydroxyphenyl)-N-(1-methyl-3-phenylpropyl)serine N',N'-diethylcarbamoylmethyl ester (1) DL-Threo-3-(3,4-dibenzyloxyphenyl)-N-benzyloxycarbonylserine (10.55 g) is dissolved in N,N-dimethylformamide (100 ml), and thereto are added isopropyl bromide (7.4 g), sodium iodide (9.0 g) and sodium hydrogen carbonate (5.04 g). The mixture is heated with stirring at 50° C. for 15 hours, and to the reaction mixture are additionally added isopropyl bromide (2.5 g), sodium iodide (3.0 g) and sodiun hydrogen carbonate (1.33 g), and the mixture is further heated with stirring at 65° C. for 24 hours. To the reaction mixture is added water, and the mixture is extracted with ethyl acetate. The organic layer is washed with saturated aqueous sodium hydrogen carbonate and saturated aqueous sodium chloride, dried, and concentrated under reduced pressure to give DL-threo-3-(3,4-dibenzyloxyphenyl)-N-benzyloxycarbonylserine isopropyl ester (Compd. No. 157) (10.8 g), m.p. 99°–100° C.

(2) The compound No. 157 obtained above (10.4 g) is dissolved in isopropyl alcohol (250 ml) and acetic acid (2.1 ml), and the mixture is subjected to hydrogenolysis in the presence of 5% Pd/C catalyst (2.0 g, 53% moist) under atmospheric pressure. After completion of the reaction (7 hours), the catalyst is filtered off to give crude DL-threo-3-(3,4-dihydroxyphenyl)serine isopropyl ester. The solution of this compound in isopropyl alcohol is used as it stands to the subsequent reaction.

(3) To the solution of the above compound in isopropyl alcohol are added benzylacetone (3.63 g) and molecular sieves 3A (5 g), and the mixture is ice-cooled and thereto is further added sodium cyanoborohydride (2.41 g). The mixture is stirred at room temperature for 2 days. The reaction mixture is filtered through celite, and the filtrate is concentrated under reduced pressure. To the residue is added water, and the mixture is extracted with ethyl acetate. The organic layer is washed with saturated aqueous sodium chloride, dried and concentrated. The residue is subjected to silica gel column chromatography (eluent, chloroform/isopropyl alcohol =15/1) to give DL-threo-3-(3,4-dihydroxyphenyl)-N-(1-methyl-3-phenylpropyl)serine isopropyl ester (Compd. No. 158) (4.7 g) as an oily mixture of diastereomers.

IR $\gamma$(film) cm$^{-1}$:3600–2400 (brs), 2970, 1720, 1605, 1445, 1360, 1140–1290, 1100, 1045, 965, 945, 865, 815.

(4) In the same manner as described in the above (1), DL-threo-3-(3,4-dibenzyloxyphenyl)-N-benzyloxycarbonylserine is treated with N,N-diethylchloroacetamide to give DL-threo-3 (3,4-dibenzylrxyphenyl)-N-benzyloxycarbonylserine N',N'-diethylcarbamoylmethyl ester (Compd. No. 159), m.p. 111°–112° C.

(5) The compound No. 159 obtained above is subjected to hydrogenolysis in the same manner as described in the above (2) to give crude DL-threo-3-(3,4-dihydroxyphenyl)serine N',N'-diethylcarbamoylmethl ester, which is used in the next reaction without any purification.

(6) The compound obtained above is reductively alkylated with benzylacetone in the same manner as described in the above (3) except that N,N-dimethylformamide is added as a cosolvent. The product is purified by flash column chromatography on silica gel to give DL-threo-3-(3,4-dihydroxyphenyl)-N-(1-methyl-3-phenylpropyl)serine N',N'-diethylcarbamoylmethyl ester (Compd. No. 160), m.p. 103°–105° C. (in HCl salt).

EXAMPLE 10

DL-Threo-3-(3,4-dihydroxyphenyl)-N-(1-methyl-3-phenylpropyl)serine carbethoxymethyl ester and DL-threo-3-(3,4-dihydroxyphenyl)-N-1-methyl-3-phenylpropyl)serine carbamoylmethyl ester (1) DL-Threo-3-(3,4-dibenzyloxyphenyl)-N-benzyloxycarbonylserine (10.56 g), sodium iodide (0.2 g) and dicyclohexylamine (4 ml) are added to dry dimethylformamide (40 ml), and thereto is further added ethyl chloroacetate (2.41 g), and the mixture is stirred at room temperature overnight. The reaction mixture is filtered to remove the precipitates, and the filtrate is concentrated under reduced pressure. The residue is dissolved in ethyl acetate, and the solution is washed with 1N hydrochlcric acid, saturated aqueous sodium hydrogen carbonate and water, dried over magnesium sulfate, and then ethyl acetate is distilled off under reduced pressure to give DL-threo-3-(3,4-dibenzyloxy-phenyl)-N-benzyloxycarbonylserine carbethoxymethyl ester (Compd. No. 161) (11.43 g), m.p. 118°–121° C.

(2) The compound No. 161 obtained above (11.31 g) is dissolved in isopropyl alcohol (100 ml), and thereto are added 5% Pd/C (1.13 g, 50% moist) and conc. hydrochloric acid (2 ml), and the mixture is subjected to catalytic reduction under hydrogen. After confirming the stop of absroption of hydrogen, Pd/C is filtered off, and the filtrate is distilled under reduced pressure to remove isopropyl alcohol. To the residue is added acetonitrile, and the resulting precipitate is separated by filtration to give DL-threo-3-(3,4-dihydroxyphenyl)serine carbethoxymethyl ester hydrochloride (Comd. No. 162) (5.71 g).

NMR $\delta_{d\text{-}DMSO}^{TMS}$ (ppm): 1.2 (t, 3H), 3.95–4.3 (m, 3H), 4.7 (s, 2H), 4.9 (d, 1H), 6.5–6.9 (m, 3H).

(3) The compound No. 162 obtained above (3.0 g) and benzylacetone (1.12 are added to isopropyl alcohol (50 ml), and the mixture is cooled to 0° to 5° C. To the mixture is added sodium cyanoborohydride (0.84 g) at 0° to 5° C. After the mixture is stirred at room temperature for 3 days, isopropyl alcohol is distilled off under reduced pressure. To the residue is added saturated aqueous sodium hydrogen carbonate, and the mixture is eztracted with ethyl acetate. The ethyl acetate layer is washed with saturated aqueous sodium chloride, dried over magnesium sulfate, and then distilled to remove ethyl acetate. The residue is purified by subjecting to silica gel chromatography to give oily DL-threo-3-(3,4-dihydroxyphenyl)-N-(1-methyl-3-phenylpropyl)serine carbethoxyethyl ester (Compd. No. 163) (2.4 g).

IR $\gamma$(film) cm$^{-1}$:3600–3000, 1740, 1610, 1510, 1450, 1380, 1280, 1240–1150, 1110, 1060.

(4) In the same manner as described in the above (1), DL-threo-3-(3,4-dibenzyloxyphenyl)-N-benzyloxycarbonylserine is reacted with chloroacetamide to give DL-threo-3(3,4-dibenzyloxyphenyl)-N-benzyloxycarbonylserine carbamoylmethyl ester (Compd. No. 164), m.p. 151°–152° C.

(5) The compound No. 164 obtained above is subjected to hydrogenolysis in the same manner as described in the above (2) to give DL-threo-3-(3,4-dihydroxypheny)serine carbamoylmethyl ester (Compd. No. 165), m.p. 65°–68° C.

(6) The compound No. 165 obtained above is reductively alkylated with benzylacetone in the same manner as described in the above (3) to give DL-threo-3-(3,4-dihydroxyphenyl)-N-(1-methyl1-3-phenylpropyl)serine carbamoylmethyl ester (Compd. No. 166), m.p. 53°–55° C.

EXAMPLE 11

DL-Threo-3-(3,4-dihydroxyphenyl)-N-(1-methyl-3-phenylpropyl)serine cyclchexyl ester and DL-threo-3-(3,4-di-hydroxyphenyl)-N-(1-methyl- 3-phenylpropyl)serine isobutyl ester (1) In the saxe manner as described in Example 9-(1), DL-threo-3-(3,4-dibenzyloxyphenyl)-N-benzyloxycarbonylserine is esterified with 3-cyclohexenyl bromide. The crude product thus obtained is subjected to silica gel column chromatography (eluent, chloroform/ethyl acetate =8/1) and crystallized from diisopropyl ether to give DL-threo-3-(3,4-dibenzyloxyhenyl)-N-benzyloxycarbonylserine 3-cyclohexenyl ester (Compd. No. 167) (2.44 g), m.p. 84°–86° C.

(2) The compound No. 167 obtained above (2.21 g) is subjected to hydrogenolysis and reduction of the double bond in the same manner as described in Example 9-(2), and the catalyst is filtered off to give DL-threo-3-(3,4dihydroxyphenyl)serine cyclohexyl ester. The solution of this compound in isopropyl alcohol is used as it stands for the subsequent reaction.

To the above isopropyl alcohol solution are added benzylacetone, molecular sieves 3A and further sodium cyanoborohydride, and the mixture is reacted, and the crude product thus obtained is subjected to silica gel column chromatography (eluent, n-hexane/acetone =7/3) to give DL-threo-3-(3,4-dihydroxyphenyl)-N-(1-methyl-3-phenylpropyl)serine cyclohexyl ester (Compd. No. 168) (0.71 g) as a mixture of diastereomers, m.p. 107°–108° C.

(3) In the same manner as described in the above (1) except that, β-methallyl chloride is used instead of 3-cyclohexenyl bromide, there is obtained DL-threo-3-(3,4-dibenzyloxyphenyl)-N-benzyloxycarbonylserine metallyl ester (Compd. No. 169), m.p. 88°–90° C.

(4) The compound No. 169 obtained above is subjected to catalytic reduction and subsequent reductive alkylation with benzylacetone in the same manner as described in Example 10-(2) and -(3) to give DL-threo-3-(3,4-dihydroxyphenyl)-N-(1-methyl-3-phenylpropyl)serine isobutyl ester (Compd. No. 170), m.p. 90°–92° C.

EXAMPLE 12

DL-Threo-1-(3,4-dihydroxyphenyl)-2-(1-methyl-3-phenylpropyl)amino-3-methyl-1,3-butanediol and DL-threo-1-(3,4-dihydroxyphenyl)-2-isopropylamino-3-methyl-1,3-butanediol (1) Magnesium (1.8 g) is added to dry ether (10 ml), and thereto is added dropwise a part of a solution of methyl iodide (11.3 g) in dry ether (50 ml), and after confirming the start of the reaction, the remaining methyl iodide solution is added dropwise at reflux temperature of ether. After the addition, the mixture is further refluxed for 1 hour, and thereto is added the compound No. 117 obtained in Example 5-(2) (4.0 g) at below 10° C. The mixture is further refluxed for 2 hours, and the reaction mixture is added to aqueous ammonium chloride. The mixture is extracted with ethyl acetate, and the extract is washed with saturated aqueous sodium chloride, dried over magnesium sulfate, and then ethyl acetate is distilled off under reduced pressure. The crude product is subjected to silica gel column chromatography (eluent: chloroform/methanol =100/5) to give DL-threo-1-(3,4-dibenzyloxyphenyl)-2-(1-methyl-3-phenylpropyl)amino-3-methyl-1,3-butanediol (diastereomer-I) (Compd. No. 171) (1.13 g), m.p. 72°–74° C.

(2) The compound No. 171 obtained above (1.0 g) is added to methanol (10 ml) and thereto is added 5% Pd/C (0.1 g, 50% moist), and the mixture is subjected to catalytic reduction under hydrogen. After confirming the stop of absorption of hydrogen, Pd/C is filtered off, and the filtrate is distilled under reduced pressure to remove methanol to give DL-threo-1-(3,4-dihydroxyphenyl)-2-(1-methyl-3-phenylpropyl)amino-3-methyl-1,3-butanediol (diastereomer-I) (Compd. No. 172) (0.51 g), which is diastereomerically single, m.p. 66°–68° C.

The compound No. 172 can also be prepared by using a free carboxylic acid obtained in Example 16-(1) instead of the above methyl ester (Compd. No. 117) as the starting material in the above procedure.

(3) In the same manner as described in the above (1) except that the compound No. 148 is used instead of the compound No. 117, there is obtained DL-threo-1-(3,4-di-benzyloxyphenyl)-2-isoprcpylamino-3-methyl-1,3-butanediol (Compd. No. 173), m.p. 101°–103° C.

(4) The compound No. 173 obtained above is subjected to debenzylation in the same manner as described in the above (2) to give DL-threo-1-(3,4-dihydroxyphenyl)-2-isopropylamino-3-methyl-1,3-butanediol (Compd. No. 174), m.p. 188°–190° C. (in ½ fumarate).

EXAMPLE 13

DL-Threo-1-(3,4-dihyroxyphenyl)-2-isopropylamino-3-methyl-1,3-butanediol (1) To a solution (27 ml) of methylmagnesium iodide in tetrahydrofuran, which is prepared from magnesium (0.73 g) and methyl iodide (4.7 g), is added a solution of DL-threo-3-(3,4-dibenzyloxyphenyl)serine (1.4 g) in the same solvent (10 ml), and the mixture is treated in the same manner as described in Example 12-(1) to give oily DL-threo-1-(3,4-dibenzyloxyphenyl)-2-amino-3-methyl-1,3butanediol (Compd. No. 175) (1.0 g, m.p. 150°–157° C., in ½ fumarate).

The compound No. 175 can also be obtained from the compound No. 116 obtained in Example 5-(1) by the same Grignard reaction as described in the above (1).

(2) The oily compound obtained above (0.90 g) is reductively alkylated with acetone in the same manner as described in Example 7 to give DL-threo-1-(3,4-dibenzyloxy-phenyl)-2-isopropylamino-3-methyl-1,3-butanediol (Compd. No. 173), (0.74 g), m.p. 100°–103° C. This compound is subjected to debenzylation to give DL-threo-1-(3,4-dihydroxyphenyl)-2-isopropylamino-3-methyl-1,3-butanediol (Compd. No. 174), (0.22g, m.p. 186°–191° C. in ½ fumarate).

EXAMPLE 14

DL-Threo-3-(3,4-dihydroxyphenyl)-N-(1-methyl-3phenylpropyl)serine amide and DL-threo-3-(3,4-dihydroxy-phenyl)-N-(1-methyl-3-phenylpropyl)serine hydrazide (1) To DL-threo-3-(3,4-dibenzyloxyphenyl)-N-(1-methyl-3-phenylpropyl)serine methyl ester (diastereomer-I) (Compd. No. 117) obtained in Example 5-(2) (7.63 g) is added methanol (88 ml) saturated with ammonia, and the mixture is stirred in an autoclave at 50° C. for 30 hours. The reaction mixture is concentrated, and the residue is purified by silica gel column chromatography (eluent, chloroform/acetcne =2/1) to give DL-threo-3-(3,4-dibenzyloxyphenyl)-N-(1-methyl-3-phenylpropyl)serine amide (Compd. No. 176) (5.6 g), m.p. 104° C.

(2) The compound No. 176 obtained above (whole amount) is dissolved in methanol (240 ml) and the mixture is hydrogenolyzed in the presence of 5% Pd/C catalyst (0.3 g, 53% moist) under atmospheric pressure. After 4 hours, the catalyst is filtered off, and the filtrate is concentrated. The residue is crystallized from methylene chloride to give DL-threo-3-(3,4-dihydroxphenyl)-N-(1-methyl-3-phenylpropyl)serine amide (Comd. No. 177) (3.18 g), m.p. 115°–117° C., which is diastereomerically single.

(3) The compound No. 117 is reacted with hydrazine hydrate in hot methanol to give DL-threo-3-(3,4-dibenzyloxyphenyl)-N-(1-methyl-3-phenylpropyl)serine hydrazide as paste. This compound is debenzylated in the same manner as described in the above (2) to give DL-threo-3-(3,4-dihydroxyphenyl)-N-(1-methyl-3-phenylpropyl)serine hydrazide (diastereomer-I) (Compd. No. 178), m.p. 140°–143° C.

EXAMPLE 15

DL-Threo-3-(3,4-dihydroxyphenyl)-N-(1-methyl-3-phenylpropyl)serine isopropylidenehydrazide DL-Threo-3-(3,4-dibenzyloxyphenyl)-N-(1-methyl-3-phenylpropyl)serine hydrazide, which is prepared from the compound No. 117 (1.62 g) in the same manner as described in Example 14, is dissolved in acetone (50 ml) in the presence of silica gel. The mixture is reacted for 2 hours and filtered. The filtrate is concentrated to give crude DL-threo-3-(3,4-dibenzyloxyphenyl)-N-(1-methyl-3-phenylpropyl)serine isopropylidenehydrazide.

The compound obtained above (whole amount) is dissolved in methanol (100 ml), and the mixture is hydrogenolyzed in the presence of 5% Pd/C catalyst (0.17 g, 53% moist) under atmospheric pressure for 4 hours. The catalyst is filtered off, and the filtrate is concentrated. The residue is recrystallized from benzene (150 ml) to give the title compound (Compd. No. 179) (0.80 g), m.p. 110°–112° C.

EXAMPLE 16

DL-Threo-3-(3,4-dihydroxyphenyl)-N-(1-methyl-3-phenylpropyl)serine (1) The compornd No. 117 (2 g) is added to methanol (9 ml) and water (1 ml), and the mixture is cooled to 0° to 10° C., and thereto is added sodium hydroxide (0.44 g), and the mixture is stirred at room temperature for 7 hours. The reaction mixture is adjusted to pH 6, and the precipitate is separated by filtration and recrystallized from dimethylsulfoxide to give DL-threo-3-(3,4-dibenzyloxyphenyl)-N-(1-methyl-3-phenylpropyl)serine (diastereomer-I) (Compd. No. 180) (1.01 g), m.p. 181° C. (decomp.)

(2) The compound No. 180 obtained above (0.9 g) is added to methanol (9 ml) and thereto is added conc. hydrochloric acid (1.7 ml) to dissolve the mixture. To the mixture is added 5% Pd/C (0.1 g, 50% moist), and the mixture is subjected to catalytic reduction under hydrogen. After confirming the stop of absorption of hydrogen, Pd/C is filtered off, and the filtrate is adjusted to pH 6. After distilling off methanol, ethanol is added to the residue, and insoluble materials are filtered off. The filtrate is again distilled to remove ethanol to give DL-threo-3-(3,4-dihydroxyphenyl)-N-(1-methyl-3-phenylpropyl)serine (diastereomer-I) (Compd. No. 181) (0.27 g), m.p. 125° C. (decomp.)

EXAMPLE 17

DL-Threo-1-(3,4-dihydroxyphenyl)-2-(1-methyl-3-phenylpropyl)amino-1,3-propanediol and DL-threo-1-(3,4-dihydroxyphenyl)-2-isopropylamino-1,3-propanediol (1) The compound No. 117 (5.0 g) is added to absolute ethanol (50 ml), and thereto is added sodium borohydride (1.4 g). The mixture is cooled to −5° C., and thereto is added dropwise a solution of calcium chloride (2.05 g) in absolute ethanol (50 ml) at −5° C. After the addition, the mixture is stirred at 0° to 5° C. for 2 hours. The reaction mixture is poured into water (1 liter). The precipitate is separated by filtration and dissolved in ethyl acetate. The solution is washed with water, dried over magnesium sulfate and then ethyl acetate is distilled off under reduced pressure to give DL-threo-1-(3,4-dibenzyloxyphenyl)-2-(1-pressure methyl-3-phenylpropyl)amino-1,3-propanediol (diastereomer-I) (Compd. No. 182) (4.62 g), m.p. 76°–78° C.

(2) The compound No. 182 obtained above (1.0 g) is dissolved in methanol (10 ml), and thereto is added 5% Pd/C (0.2 g, 50% moist), and the mixture is subjected to catalytic reduction under hydrogen. After confirming the stop of absorption of hydrogen, Pd/C is filtered off, and methanol is distilled off under reduced pressure. To the residue are added acetone and oxalic acid (0.19 g), and the precipitate is separated by filtration to give DL-threo-1-(3,4-dihydroxyphenyl)-2-(1-methyl-3-phenylpropyl)amino-1,3-propanediol ½ oxalate (Compd. No. 183) (0.24 g), m.p. 120° C.

(3) The compou.nd No. 148 obtained in Example 7 is reduced by calcium borohydride in the same manner as described in the above (1) to give DL-threo-1-(3,4-dibenzyl-oxyphenyl)-2-isopropylamino-1,3-propanediol (Compd. No. 184), m.p. 84°–86° C.

(4) The compound No. 184 obtained above is subjected to hydrogenolysis n the same manner as described in the above (2) to give DL-threo-1-(3,4-dihydroxyphenyl)-2-isopropylamino-1,3-propanediol (Compd. No. 185), m.p. 158°–163° C. (in HCl salt).

EXAMPLE 18

DL-Threo-1-(3,4-dihydroxyphenyl)-2-(1-methyl-3-phenylpropyl)amino-1,3-propanediol (1) The compound No. 116 (8.60 g) is treated with calcium borohydride, which is prepared from sodium borohydride (3.78 g) and calcium chloride (5.66 g), in the same manner as described in Example 17-(1) to give DL-threo-1-(3,4-dibenzyloxyphenyl)-2-amino-1,3-propanediol (Compd. No. 186) (6.7 g, m.p. 165°–167° C. as HCl salt).

(2) The HCl salt of the compound No. 186 (4.16 g) is hydrogenolyzed in the same manner as described in Example 17-(2) to give crude DL-threo-1-(3,4-dihydroxyphenyl)-2-amino-1,3-propanediol hydrcchloride, which is used in the next reaction without any purification.

(3) The compound obtained above is reductively alkylated with benzylacetone (2.3 ml) in the same manner as described in Example 3-(3) to give the title compound (Compd. No. 187) (0.82 g, m.p. 99°–101° C. as HCl salt) as a mixture of diastereoisomers.

EXAMPLE 19

DL-Threo-1-(3,4-dihydroxyphenyl)-2-(1-methyl-3-phenylpropyl)amino-3-(N-methylcarbamoyl)oxypropanol and DL-threo-1-(3,4-dihydroxyphenyl)-2-(1-methyl-3-phenylpropyl)-amino-3-carbamoyloxypropanol (1) To a solution of the compound No. 182 (512 mg) in tetrahydrofuran are added methyl isocyanate (70 mg) and trifluoroacetic acid (171 mg) at room temperature, and the mixture is stirred fcr 2 days. To the mixture is added saturated aqueous sodium hydrogen carbonate, and the mixture is extracted with methylene chloride. The organic layer is washed with water three times, dried over anhydrous sodium sulfate, and concentrated under reduced pressure. The residue is subjected to preparative silica gel thin layer chromatography to give DL-threo-1-(3,4-dibenzyloxy-phenyl)-2-(1-methyl-3-phenylpropyl)amino-3-(N-methylcarbamoyl)oxypropanol (491 mg). This compound is debenzylated in the same manner as described in Example 17-(2) to give DL-threo-1-(3,4-dihydroxyphenyl)-2-(1-methyl-3-phenyl-propyl)amino-3-(N-methylcarbamoyl)oxypropanol (Compd. No. 188), m.p. 95°–99° C.

(2) In the same manner as described in the above (1) except that the compound No. 182 is reacted with sodium cyanate, followed by debenzylation, there is obtained DL-threo-1-(3,4-dihydroxyphenyl)-2-(1-methyl-3-phenylpropyl)-amino-3-carbamoyloxypropanol (Compd. No. 189), m.p. 53°–55° C.

EXAMPLE 20

DL-Erythro-1-(3,4-dihydroxyphenyl)-2-methylamino-1,3-propanediol (1) DL-Erythro-3-(3,4-dibenzyloxyphenyl)-N-benzyloxycarbonylserine (1.6 g) is dissolved in dry tetrahydrofuran (12 ml), and the mixture is ice-cooled. To the solution is added lithium: aluminum hydride (0.35 g), and the mixture is reacted at room temperature for 1 hour and further at 50° to 55° C. for 2 hours. The reaction mixture is cooled, and thereto are added ether (150 ml), methanol (2 ml) and water (2.5 ml), and the insoluble materials are filtered off. The organic layer is separated, dried, and then the solvent is distilled off to give oily DL-erythro-1(3,4-dibenzyloxyphenyl)-2-methylamino-1,3-propanediol (Compd. No. 190) (1.4 g).

IR $\gamma$(film) cm$^{-1}$: 3300–3500, 1600, 1510, 1450, 1430, 1380, 1270, 1220, 1130, 1100.

(2) The compound No. 190 obtained above (0.7 g) is subjected to catalytic reduction in a usual manner, and crystallized from ethyl acetate to give DL-Erythro-1-(3,4-dihydroxyphenyl)-2-methylamino-1,3-propanediol (Compd. No. 191) (0.26 g), m.p. 77°–80° C.

EXAMPLE 21

DL-Threo-1-(3,4-dihydroxyphenyl)-2-(1-methyl-3-phenylpropyl)amino-3-aminopropanol To a solution of lithium aluminum hydride (1.53 g) in tetrahydrofuran (50 ml) is added a solution of the compound No. 176 (3.53 g) in the same solvent (30 ml) over 20 minutes without cooling, and the mixture is refluxed for 6 hours. The reaction mixture is quenched by a successive addition of water (1.53 ml), 15% aqueous sodium hydroxide (1.53 ml) and water (1.53 ml). The precipitate is filtered off, and the filtrate is concentrated. The residue is subjected to silica gel column chromatography (eluent, tetrahyrofuran containing 0.5% conc. aqueous ammonia) to give oily DL-threo-1-(3,4-dibenzyloxyphenyl)-2-(1-methyl-3-phenylpropyl)amino-3-amiropropanol (2.23 g). This compound is debenzylated at room temperature and atmospheric pressure in the presence of 5% P/C (50% moist) in methanol (100 ml) containing ca. 2 molar equivalent of hydrochloric acid. After uptake of hydrogen is ceased, the catalyst is removed and the solvent is distilled off. The residue is triturated with ether and the precilitate is separated by filtration to give the title compound as hydrochloride (Compd. No. 192) (0.91 g), m.p. 130°–150° C.

EXAMPLE 22

DL-Threo-3-(3,4-dihydroxyphenyl)-N-(1-methyl-3phenylpropyl)serine pyrrolidine amide.

(1) The compound No. 8 (855 mg) is condensed with pyrrolidine via the mixed anhydride in the same manner as described in Example 3-(1). The crude product is purified by silica gel column chromatography (eluent: chloroform/methanol=100/3) to give DL-threo-3-(3,4-dibenzyloxy-phenyl)-N-t-butoxycarbonylserine pyrrolidine amide as an amorphous solid (Compd. No. 193).

NMR$\delta_{CDCl_3}^{TMS}$ (ppm): 1.33 (s, 9H), 1.4–2.0 (m, 4H), 2.7–3.6 (m, 4H), 4.25 (br s, 1H), 4.41 (dd, 1H), 4.84 (br d, 1H), 5.09 & 5.11 (s, 2H+2H), 5.58 (d,1H), 6.83 & 7.08 (s, 2H+1H), 7.2–7.5 (m, 1OH).

(2) The compound No. 193 (580 mg) obtained above is dissolved in ethanol (10 ml), and thereto is added 15% HCl solution of isopropyl alcohol (10 ml) and the mixture is stirred at room temperature. After confirming the completion of the reaction, the solvent is evaporated and the residue is triturated with ether to give DL-threo-3-(3,4-dibenzyloxyphenyl)serine pyrrolidine amide hydrochloride (Compd. No. 194) (440 mg, m.p. 178° C).

(3) The compound No. 194 obtained above is reductively alkylated with benzylacetone in the same manner as described in Example 3-(3). The crude product is purified by silica gel colum chromatography to give DL-threo-3-(3,4-dibenzyloxyphenyl)-N-(1-methyl-3-phenylpropyl)serine pyrrolidine amide (Compd. No. 195). This compound is hydrogenolyzed in a usual way to give the compound No. 19.

EXAMPLE 23

DL-Threo-1-(3,4-dihydroxyphenyl)-2-(1-methyl-3-phenylpropyl)amino-3-pyrrolidinopropanol The hydrochloride salt of the compound No. 19 (435 mg) in tetrahydrofuran (10 ml) is treated with sodium borohydride (380 mg) at ice-water temperature. After 10 min., to the mixture is added a solution of boron trifluoride etherate (1.23 ml) in tetrahydrofuran (10 ml) at the same temperature over 30 min. After stirring at room temperature overnight, the reaction mixture is quenched with water, and 10% hydrochloric acid is added to adjust pH below 0.5. The mixture is refluxed for 50 min., made alkaline with solid sodium bicarbonate and extracted with ethyl acetate. The extract is washed with brine, dried over anhydrous sodium sulfate and concentrated. The residue is subjected to silica gel column chromatography (eluent:acetonitrile/acetic acid/water=9/1/1) to give the title compound (Compd. No. 196) (84 mg, m.p. 125° C (dec.) in HCl salt).

The invention being thus described, it will be obvious that the same may be varied in many ways. Such variations are not be regarded as a departure from the spirit and scope of the invention, and all such modifications as would be obvious to one skilled in the art are intended to be included within the scope of the following claims.

What is claimed is:

1. A phenylserine derivative of the formula:

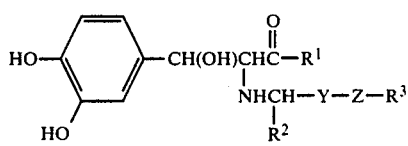

wherein R$^1$ is a member selected from the group consisting of

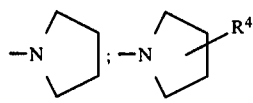

wherein R$_4$ is C$_1$–C$_4$ alkyl, carboxyl, carbo(C$_1$–C$_4$)alkoxy, hydroxy(C$_1$–C$_4$)alkyl, phenyl or $$-COOCH_2-\phenyl\quad;\quad -N\text{(isoindoline)}\ ;$$

$$\text{(indoline)}\ ;\ \text{and}\ \text{(octahydroindole)}\ ;$$

wherein
 $R^2$ is hydrogen, a $C_1$–$C_4$ alkyl group, or phenyl;
 $R^3$ is hydrogen; a $C_1$–$C_4$ alkyl group; a $C_5$–$C_6$ cycloalkyl group; unsubstituted pehnyl, phenyl having one or more substituents selected from the group consisting of a $C_1$–$C_4$ alkyl group, hydroxy, $C_1$–$C_4$ alkoxy, halogen, trifluoromethyl, di($C_1$–$C_4$ alkyl)amino and methlenedioxy; naphtyl; furyl, thienyl; pyrrolyl; or indolyl;
 Y is a single bond; an unsubstituted $C_1$–$C_4$ alkylene; or a $C_1$–$C_4$ alkylene substituted by a $C_1$–$C_4$ alkyl or phenyl;
 Z is a single bond; oxa; thia; $C_1$–$C_4$ alkylimino; or —CONH—; or
the group Z—$R^3$ forms a 1,4-benzodioxyanyl group, or the group $$R^2-\overset{|}{C}H-YZR^3$$

forms a tetrahydronaphthyl group, with the proviso that when Y and Z both represent a single bond, it is the same single bond, or a pharmaceutically acceptable acid addition salt thereof.

2. A phenylserine derivative according to claim 1, which is represented by the formula:

$$HO-\phenyl(HO)-CH(OH)CH(NHCH(CH_2)_nZR^3\,|\,R^2)-\overset{O}{\overset{\|}{C}}R^1$$

wherein
 $R^1$ is as defined in claim 11; $R^2$ is hydrogen; $C_1$–$C_4$ alkyl; or phenyl;
 n is an integer of 1 to 4;
 Z is a single bond; oxa; thia; $C_1$–$C_4$ alkylamino; or —CONH—;
 $R^3$ is $C_1$–$C_4$ alkyl; $C_5$–$C_6$ cycloalkyl; unsubstituted phenyl; phenyl having one or more subsituents selected from the group consisting of $C_1$–$C_4$ alkyl, hydroxy, $C_1$–$C_4$ alkoxy, halogen, trifluoromethyl, di($C_1$–$C_4$ alkyl)amino and methylenedioxy; 1-or 2-naphtyl; 2-or 3-furyl; 2- or 3-thienyl; or 2- or 3-pyrrolyl; or the group $$R^2\overset{|}{C}H(CH_2)_nZR^3$$

forms a tetrahydronaphthyl group; or a pharmaceutically acceptable acid addition salt thereof.

3. A phenylserrine derivative according to claim 2, wherein $R^1$ is $$-N\text{(pyrrolidine)}$$

4. A phenylserine derivative according to claim 3, which is represented by the formula:

$$HO-\phenyl(HO)-CH(OH)CHCON\text{(pyrrolidine)}\,|\,NHCHCH_2CH_2-\phenyl\,|\,CH_3$$

5. A phenylserine derivative according to claim 2, which is represented by the formula:

$$HO-\phenyl(HO)-CH(OH)CHCON\text{(pyrrolidine)}\,|\,NH(CH_2)_3-\phenyl$$

6. A phenylserine derivative according to claim 3, wherein $R^3$ is cyclohexyl, phenyl, or a phenyl substituted with at least one member selected from the group consisting of a $C_1$–$C_4$ alkyl, hydroxy, a $C_1$–$C_4$ alkoxy, a halogen, trifluromethyl, a di($C_1$–$C_4$)alkyl amino and methylenedioxy.

7. A phenylserine derivative according to claim 2, wherein $R^3$ is a member selected from the group consisting of 1-naphthyl, 2-napthyl, 2-furyl, and 3-furyl.

8. A phenylserine derivative according to claim 1, wherein the group Z-$R^3$ forms a 1,4 -benzodioxanyl group or the $$R^2\overset{|}{C}HYZR^3$$

forms a tetrahydronaphthyl group.

9. A phenylserine derivative according to claim 1, wherein $R^1$ is a member selected from the group consisting of:

$$-N\text{(isoindoline)}\ ,\ \text{(indoline)}\ ,\ \text{and}\ \text{(octahydroindole)}\ .$$

10. A pharmaceutical composition for the treatment of allergic diseases induced by SRS-A which comprises as an essential active ingredient a therapeutically effective amount of the compound according to claim 1 in admixture with a pharmaceutically acceptable carrier or diluent.

11. A method for the treatment of allergic diseases induced by SRS-A, which comprises administering a therapeutically effective amount for the prophylaxis and treatment of allergic diseases induced by SRS-A of the compound according to claim 1 to a person suffering from said allergic diseases.

* * * * *